(12) United States Patent
Benedict et al.

(10) Patent No.: US 9,745,370 B2
(45) Date of Patent: Aug. 29, 2017

(54) ANTIBODIES TO SERICIN AND METHODS AND KITS USING SAME

(71) Applicant: Cerapedics, Inc., Westminster, CO (US)

(72) Inventors: James J. Benedict, Detroit Lakes, MN (US); Tristan Stuart Barnes, Louisville, CO (US); Claude George Lerner, Highland Park, IL (US)

(73) Assignee: Cerapedics, Inc., Westminster, CO (US)

( * ) Notice: Subject to any disclaimer, the term of this patent is extended or adjusted under 35 U.S.C. 154(b) by 0 days.

(21) Appl. No.: 15/125,780

(22) PCT Filed: Mar. 12, 2015

(86) PCT No.: PCT/US2015/020248
§ 371 (c)(1),
(2) Date: Sep. 13, 2016

(87) PCT Pub. No.: WO2015/138772
PCT Pub. Date: Sep. 17, 2015

(65) Prior Publication Data
US 2017/0015736 A1 Jan. 19, 2017

Related U.S. Application Data

(60) Provisional application No. 61/953,098, filed on Mar. 14, 2014.

(51) Int. Cl.
| | | |
|---|---|---|
| *C07K 16/18* | (2006.01) | |
| *G01N 33/53* | (2006.01) | |
| *A61L 27/22* | (2006.01) | |
| *A61L 27/36* | (2006.01) | |
| *A61L 27/50* | (2006.01) | |
| *G01N 33/68* | (2006.01) | |
| *C07K 14/435* | (2006.01) | |
| *A61L 15/40* | (2006.01) | |
| *D01B 7/00* | (2006.01) | |

(52) U.S. Cl.
CPC ............ *C07K 16/18* (2013.01); *A61L 27/227* (2013.01); *A61L 27/3608* (2013.01); *A61L 27/50* (2013.01); *G01N 33/53* (2013.01); *G01N 33/6878* (2013.01); *A61L 15/40* (2013.01); *A61L 2430/02* (2013.01); *C07K 14/43586* (2013.01); *C07K 2317/34* (2013.01); *D01B 7/00* (2013.01); *G01N 2333/43578* (2013.01)

(58) Field of Classification Search
None
See application file for complete search history.

(56) References Cited

U.S. PATENT DOCUMENTS

| | | |
|---|---|---|
| 4,200,690 A | 4/1980 | Root et al. |
| 6,203,999 B1 | 3/2001 | Robbins et al. |
| 2003/0134388 A1 | 7/2003 | Sasaki et al. |

OTHER PUBLICATIONS

Cell Signaling Technology, "Western Blotting Protocol," <www.cellsignal.com/common/content/content.jsp?id=western>, posted Jun. 2005, revised Nov. 2013, retrieved May 18, 2015 (4 pages).
Dash et al., "Purification and biochemical characterization of a 70 kDa sericin from tropical tasar silkworm, *Antheraea mylitta*," Comp Biochem Physiol B Biochem Mol Biol. 147(1):129-34 (2007).
International Search Report and Written Opinion for International Application No. PCT/US2015/020248, mailed Jun. 19, 2015 (11 pages).
International Preliminary Report on Patentability for International Patent Application No. PCT/US2015/020248, mailed Sep. 22, 2016 (8 pages).

*Primary Examiner* — Zachary Howard
(74) *Attorney, Agent, or Firm* — Clark & Elbing LLP; Kristina Bicker-Brady

(57) ABSTRACT

The present invention relates to antibodies that bind to a polypeptide at an epitope in the amino acid sequence of SEQ ID NO: 1 (e.g., a sericin polypeptide). The invention also provides methods and kits using the antibodies of the invention. In some embodiments, the antibody binds to a polypeptide at an epitope in the amino add sequence of SEQ ID NO: 2. In some embodiments, the antibody binds to a polypeptide at an epitope in the amino add sequence of SEQ ID NO: 3. In some embodiments, the polypeptide is a sericin polypeptide (e.g., a sericin isoform 1B polypeptide). In a related aspect, the invention features a method for selectively detecting sericin in a sample.

27 Claims, 4 Drawing Sheets

ANTIBODIES TO SERICIN AND METHODS AND KITS USING SAME

BACKGROUND OF THE INVENTION

Silk from the silkworm *Bombyx mori* is a versatile biomaterial that has been valued for its use in the medical, research, cosmetic, and textile industries. Raw silk from the silkworm is composed primarily of two high-molecular weight proteins. The actual silk fibers are composed of fibroin polypeptides, and the "glue" that cements the fibers together is composed of sericin polypeptides. Depending on the intended utility of the raw silk, the fibroin and sericin components of silk must be separated from one another in a process known as "degumming" to obtain fibroin preparations that are substantially free of sericin and sericin preparations that are substantially free of fibroin. Silk fibroin preparations that are substantially free of sericin are preferred, for example, if the silk is desired for medical applications because the presence of sericin has been shown to produce unwanted thrombogenic and/or inflammatory responses. On the other hand, silk sericin preparations that are substantially free of fibroin are preferred, for example, if the silk is desired for certain cosmetic uses, such as for incorporation into shampoo as an additive, which has been shown to coat hair and provide a protective transparent film that improves hair luster and flexibility.

Despite the widespread utility of silk, there remains an unmet need to develop sensitive and accurate diagnostic compositions and methods for evaluating sericin content of silk materials.

SUMMARY OF THE INVENTION

The invention is in part based on the development of antibodies that bind to sericin, but not fibroin, polypeptides, which find particularly advantageous use in diagnostic methods and compositions, such as immunoassay kits.

In a first aspect, the invention features an antibody that binds to a polypeptide at an epitope in the amino acid sequence RSHHSGVNRLLHKPGQGKICLCFENIFDIPYHLRK (SEQ ID NO: 1). In some embodiments, the antibody binds to a polypeptide at an epitope in the amino acid sequence RSHHSGVNRLLHKPGQGK (SEQ ID NO: 2). In some embodiments, the antibody binds to a polypeptide at an epitope in the amino acid sequence KICLCFENIFDIPYHLRK (SEQ ID NO: 3). In some embodiments, the polypeptide is a sericin polypeptide (e.g., a sericin isoform 1B polypeptide). In some embodiments, the antibody is a polyclonal antibody. In some embodiments, the antibody is a monoclonal antibody, a chimeric antibody, a synthetic antibody, a monospecific antibody, a bispecific antibody, or a multispecific antibody. In some embodiments, the antibody is an antibody fragment that binds to a polypeptide at an epitope in the amino acid sequence RSHHSGVNRLLHKPGQGKICLCFENIFDIPYHLRK (SEQ ID NO: 1). In some embodiments, the antibody fragment binds to a sericin polypeptide (e.g., a sericin isoform 1B polypeptide). In some embodiments, the antibody fragment is selected from the group consisting of Fab, Fab'-SH, Fv, scFv, and (Fab)$_2$ fragments. In some embodiments, the antibody further comprises an agent. In some embodiments, the agent is a diagnostic agent. In some embodiments, the diagnostic agent is a label. In some embodiments, the label is an electrochemiluminescent (ECL) label, an enzymatic label, a fluorescent label, or a radiolabel. In some embodiments, the ECL label is a Sulfo-TAG label (Meso Scale Discovery). In some embodiments, the enzymatic label is horseradish peroxidase (HRP). In some embodiments, the agent is directly conjugated to the antibody. In other embodiments, the agent is indirectly conjugated to the antibody by a linker.

In a related aspect, the invention features a method for selectively detecting sericin in a sample, the method comprising the steps of: (a) immobilizing the sample to a solid support to form an immobilized sample; (b) contacting the immobilized sample with a capture antibody to form an immobilized sericin-capture antibody complex, wherein the capture antibody binds to sericin at an epitope within residues 1148-1182 of sericin (SEQ ID NO: 1); (c) separating unbound capture antibody from the immobilized sericin-capture antibody complex; and (d) measuring the level of sericin bound to the capture antibody using a detection means for the capture antibody. In some embodiments, the capture antibody is directly detectable. In some embodiments, the capture antibody comprises an agent, such as a diagnostic agent. The diagnostic agent can be an ECL label, such as a Sulfo-TAG label, to provide a sericin ECL-based immunoassay.

In a related aspect, the invention features a method for selectively detecting sericin in a sample, the method comprising the steps of: (a) immobilizing the sample to a solid support to form an immobilized sample; (b) contacting the immobilized sample with a capture antibody to form an immobilized sericin-capture antibody complex, wherein the capture antibody binds to sericin at an epitope within residues 1148-1182 of sericin (SEQ ID NO: 1); (c) separating unbound capture antibody from the immobilized sericin-capture antibody complex; (d) contacting the immobilized sericin-capture antibody complex with a detectable antibody that binds the capture antibody to form an immobilized sericin-capture antibody-detectable antibody complex; (e) separating unbound detectable antibody from the immobilized sericin-capture antibody-detectable antibody complex; and (f) measuring the level of sericin bound to the capture antibody using a detection means for the detectable antibody. In some embodiments, the detectable antibody is directly detectable. In some embodiments, the detectable antibody comprises an agent, such as a diagnostic agent. The diagnostic agent can be an enzymatic label, such as HRP, to provide a sericin antigen-down enzyme-linked immunosorbent assay (ELISA).

In a related aspect, the invention features a method for selectively detecting sericin in a sample, the method comprising the steps of: (a) immobilizing a capture antibody to a solid support to form an immobilized capture antibody, wherein the capture antibody binds to sericin at an epitope within residues 1148-1182 of sericin (SEQ ID NO: 1); (b) contacting the immobilized capture antibody with the sample to form an immobilized capture antibody-sericin complex; (c) separating unbound sample from the immobilized capture antibody-sericin complex; (d) contacting the immobilized capture antibody-sericin complex with a detectable antibody that binds to sericin at an epitope within residues 1-1147 of sericin (SEQ ID NO: 4) or residues 1182-1186 of sericin (SEQ ID NO: 5) to form an immobilized capture antibody-sericin-detectable antibody complex; (e) separating unbound detectable antibody from the immobilized capture antibody-sericin-detectable antibody complex; and (f) measuring the level of sericin bound to the capture antibody using a detection means for the detectable antibody. In some embodiments, the detectable antibody comprises an agent, such as a diagnostic agent. The diagnostic agent can be an enzymatic label, such as HRP, to provide a sericin sandwich ELISA.

In a related aspect, the invention features an immunoassay kit for selectively detecting sericin in a sample, wherein the immunoassay kit comprises: (a) a capture antibody that binds to sericin at an epitope within residues 1148-1182 of sericin (SEQ ID NO: 1); and (b) a solid support. In some embodiments, the sample is immobilized on the solid support. When the sample is immobilized on the solid support, in some embodiments, the capture antibody is directly detectable, for example, by a Sulfo-TAG label. In some embodiments, the kit further comprises a detectable antibody that binds the capture antibody. In some embodiments, the detectable antibody is directly detectable, for example, by a HRP label. In some embodiments, the detectable antibody is directly detectable, for example, by a HRP label, and the capture antibody is not directly detectable. In other embodiments, capture antibody is immobilized to the solid support. When the capture antibody is immobilized on the solid support, in some embodiments, the kit further comprises a detectable antibody that binds to sericin at an epitope within residues 1-1147 of sericin (SEQ ID NO: 4) or residues 1182-1186 of sericin (SEQ ID NO: 5). In some embodiments, the detectable antibody is directly detectable, for example, by a HRP label.

In any one of the above detection methods or immunoassay kits, the sample can be silk.

In any one of the above detection methods or immunoassay kits, the solid support can be a microtiter plate. In some embodiments, the microtiter plate comprises polystyrene.

In any one of the above detection methods or immunoassay kits, the sensitivity for sericin can be ≤100 ng/ml (e.g., ≤50 ng/ml, ≤10 ng/ml, ≤5 ng/ml, ≤1 ng/ml, ≤0.1 ng/ml, ≤0.01 ng/ml, or ≤0.001 ng/ml). In some embodiments, the sensitivity for sericin is ≤1 ng/ml.

In any one of the above detection methods or immunoassay kits, the detection limit for sericin can be ≤5% (e.g., ≤1%, ≤0.5%, ≤0.1%, ≤0.05%, ≤0.01%, ≤0.005%, ≤0.00125%, or ≤0.001%). In some embodiments, the detection limit for sericin is ≤1%. In some embodiments, the detection limit for sericin is ≤0.00125%.

In a related aspect, the invention features a method for inserting an implantable composition comprising silk into a subject, the method comprising: (a) providing silk fibers, wherein the silk fibers have a sericin content of ≤0.5% (w/w) measured using one or more (e.g., 1, 2, or 3 or more) of the above methods of detection and/or kits; (b) incorporating the silk fibers into the implantable composition; and (c) inserting the implantable composition into the subject.

In a related aspect, the invention features a method for inserting an implantable composition comprising silk into a subject, the method comprising: (a) providing an implantable composition comprising silk, wherein the silk has a sericin content of ≤0.5% (w/w) measured using one or more (e.g., 1, 2, or 3 or more) of the above methods of detection and/or kits; and (b) inserting the implantable composition into the subject.

In a related aspect, the invention features a method for determining whether a batch of silk is suitable for medical use, the method comprising: (a) providing a batch of silk, wherein the silk has a sericin content measured using one or more (e.g., 1, 2, or 3 or more) of the above methods of detection and/or kits; and (b) on the basis of the sericin content, determining whether the batch of silk is suitable for medical use.

In a related aspect, the invention features a method for implanting a pliable implantable composition into a subject, the pliable implantable composition comprising: (a) from 5% to 20% (w/w) (e.g., 5% to 10%, 10% to 15%, or 15% to 20% (w/w)) a dispersing agent selected from glycerin, polyethylene glycol, N-methyl pyrrolidone, and triacetin; (b) from 1.0% to 6.0% (w/w) (e.g., 1.0% to 1.5%, 1.5% to 2.5%, 2.5% to 4.5%, or 3.5% to 6.0% (w/w)) a polymer selected from sodium carboxymethylcellulose, polyvinylalcohol, hydroxyethyl cellulose, hydroxypropyl methylcellulose, hydroxyethyl methylcellulose, methylcellulose, ethylcellulose, and hyaluronic acid; (c) from 65% to 90% (w/w) (e.g., 65% to 75%, 75% to 85%, 80% to 90%, or 85% to 90% (w/w)) particulate bone graft substitute or particulate demineralized bone matrix having a mean particle size of from 100 µm to 1000 µm (e.g., 150±50, 250±50, 350±50, 450±50, 550±50 µm, 600±50 µm, or 750±250 µm); and (d) from 0.2% to 3.5% (w/w) (e.g., 0.2% to 0.6%, 0.5% to 0.9%, 0.8% to 1.2%, 1.1% to 2.0%, 1.5% to 2.2%, 1.9% to 2.7%, or 2.4% to 3.5% (w/w)) silk fibers having (i) an average length of from 0.5 to 15 mm (e.g., 0.5 to 1.5 mm, 1.0 to 3.0 mm, 2.5 to 15 mm, 4.5 to 9 mm, 7.0 to 15 mm, or 10 to 15 mm) and (ii) a sericin content of ≤0.5% (w/w) measured using one or more (e.g., 1, 2, or 3 or more) of the above methods of detection and/or kits, wherein the method comprises inserting the pliable implantable composition into the subject at an osteogenic site. The particulate bone graft substitute can be selected from hydroxyapatite particles, dahllite particles, tetracalcium phosphate particles, calcium pyrophosphate particles, tricalcium phosphate particles, calcium hydrogen phosphate particles, octacalcium phosphate particles, calcium fluorapatite particles, anorganic bone mineral, and mixtures thereof. For example, the particulate bone graft substitute can be hydroxyapatite particles having diameters between 250 microns to 425 microns. In one particular embodiment, the particulate bone graft substitute is anorganic bone mineral coated with P-15 peptide.

In a related aspect, the invention features a method for determining whether a batch of silk is suitable for use in a skin care, hair care, or hair coloring composition, the method comprising: (a) providing a batch of silk, wherein the silk has a sericin content measured using one or more (e.g., 1, 2, or 3 or more) of the above methods of detection and/or kits; and (b) on the basis of the sericin content, determining whether the batch of silk is suitable for use in the skin care, hair care, or hair coloring composition.

In a related aspect, the invention features a method for cryoprotecting cells, the method comprising: (a) providing a serum-free freezing medium, the serum-free freezing medium comprising sericin, wherein the sericin is substantially free of fibroin as measured using one or more (e.g., 1, 2, or 3 or more) of the above methods of detection and/or kits; (b) resuspending cells with the serum-free freezing medium in a cryovial; and (c) freezing the cryovial. In some embodiments, the cells are mammalian cells.

DETAILED DESCRIPTION OF EMBODIMENTS OF THE INVENTION

I. Definitions

Figure 1:
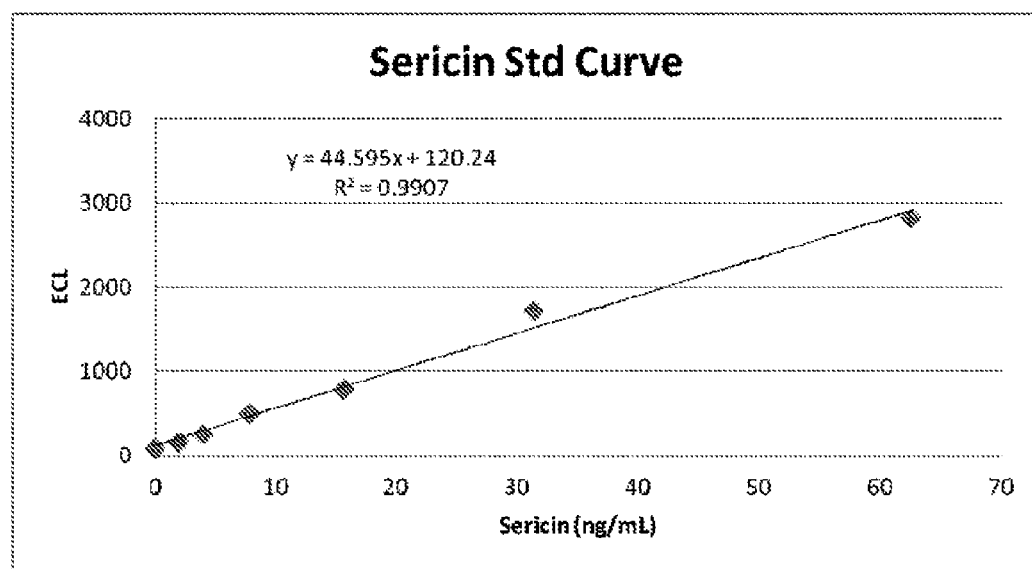
FIG. 1 is a graph showing a sericin standard curve for the electrochemiluminescent (ECL)-based sericin assay, indicating that the ECL-based assay exhibits a linear range of detection of at least 0 to 60 ng/ml, with an $R^2$ value of 0.9907.

The term "antibody" is used in the broadest sense and includes polyclonal antibodies, monoclonal antibodies (e.g., full-length or intact monoclonal antibodies), multivalent antibodies, multispecific antibodies (e.g., bispecific antibodies so long as they exhibit the desired biological activity), as well as antibody fragments (as described in greater detail herein) so long as they exhibit the desired target molecule-binding activity. An antibody typically comprises both "light chains" and "heavy chains." The light chains of antibodies (immunoglobulins) from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), for example, IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known.

An "antibody that binds" to a target polypeptide or antigen of interest (e.g., a polypeptide comprising the amino acid sequence of RSHHSGVNRLLHKPGQGKICLCFENIFDIPYHLRK (SEQ ID NO: 1), RSHHSGVNRLLHKPGQGK (SEQ ID NO: 2), and/or KICLCFENIFDIPYHLRK (SEQ ID NO: 3), e.g., a sericin polypeptide, e.g., sericin) is one that binds the target polypeptide or antigen with sufficient affinity such that the antibody is useful as a diagnostic and/or therapeutic agent in targeting the polypeptide or antigen, and does not significantly cross-react with other proteins. In such embodiments, the extent of binding of the antibody to a "non-target" protein (e.g., fibroin) will be less than about 10% of the binding of the compound to its particular target polypeptide or antigen, as can be determined, for example, by fluorescence activated cell sorting (FACS) analysis, immunohistochemistry, radioimmunoprecipitation (RIA), ELISA, or any other standard quantitative or semi-quantitative technique known in the art. In certain embodiments, an antibody that binds to a target polypeptide or antigen of interest (e.g., sericin) has a dissociation constant (Kd) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

"Antibody fragments" or "fragments" comprise only a portion of an intact antibody, wherein the portion preferably retains at least one, preferably most or all, of the functions normally associated with that portion when present in an intact antibody. Examples of antibody fragments include Fab, Fab' (e.g., Fab'-SH), F(ab')$_2$, and Fv fragments (e.g., single-chain variable fragments (scFv)); diabodies; linear antibodies; single-chain antibody molecules; and multispecific antibodies formed from antibody fragments. Papain digestion of antibodies produces two identical antigen/target molecule-binding fragments, called "Fab" fragments, each with a single antigen/target molecule-binding site, and a residual "Fc" fragment, whose name reflects its ability to crystallize readily. Pepsin treatment yields an F(ab')$_2$ fragment that has two antigen/target molecule-binding sites and is still capable of cross-linking antigen/target molecule. In one embodiment, an antibody fragment comprises an antigen/target molecule-binding site of the intact antibody and thus retains the ability to bind antigen/target molecule (e.g., a polypeptide comprising the amino acid sequence of RSHHSGVNRLLHKPGQGKICLCFENIFDIPYHLRK (SEQ ID NO: 1), RSHHSGVNRLLHKPGQGK (SEQ ID NO: 2), and/or KICLCFENIFDIPYHLRK (SEQ ID NO: 3), e.g., a sericin polypeptide, e.g., sericin).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence (e.g., "complementarity determining regions" or "CDRs") and/or form structurally defined loops (e.g., "hypervariable loops") and/or contain the antigen-contacting residues (e.g., "antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. The monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In contrast, "polyclonal antibody" preparations typically include a heterogeneous population of antibodies directed against the same epitope or different epitopes.

The term "capture antibody" refers to an antibody capable of binding and capturing a target polypeptide or antigen of interest (e.g., a polypeptide comprising the amino acid sequence of RSHHSGVNRLLHKPGQGKICLCFENIFDIPYHLRK (SEQ ID NO: 1), RSHHSGVNRLLHKPGQGK (SEQ ID NO: 2), and/or KICLCFENIFDIPYHLRK (SEQ ID NO: 3), e.g., a sericin polypeptide, e.g., sericin) in a sample such that under suitable conditions, the capture antibody-target molecule complex can be separated from the rest of the sample. In some embodiments, the capture antibody is immobilized or immobilizable.

The term "detectable antibody" refers to an antibody that is capable of being detected either directly through a label (e.g., an electrochemiluminescent (ECL) label, an enzymatic label, a fluorescent label, or a radiolabel) amplified by a detection means, or indirectly through, e.g., another antibody that is labeled. For direct labeling, the antibody is typically conjugated to a moiety that is detectable by some means. In one embodiment, the detectable antibody is conjugated to an ECL label, such as a Sulfo-TAG label (Meso Scale Discovery).

The term "detection means" refers to a moiety or technique used to detect the presence of the detectable antibody in the ELISA- or ECL-based assays described herein and includes detection agents that amplify the immobilized label. In one embodiment, the detection means is a carbon electrode excitation source that supports the electrical stimulation of the Sulfo-TAG reporter molecule, ruthenium(II) tris-bipyridal $[Ru(bpy)_3{}^{2+}]$, to emit light at 620 nm. In another embodiment, the detection means is a colorimetric detection agent, such as 3,3',5,5'-tetramethyl benzidine (TMB), which is a substrate for detection of horseradish peroxidase (HRP) in the presence of hydrogen peroxide.

An "epitope" according to this invention refers to amino acid residue(s) of a target polypeptide or antigen that contribute energetically to the binding of an antibody. The binding of the target polypeptide or antigen (e.g., a polypeptide comprising any one of SEQ ID NOs: 1-4) to the antibody can be determined, for example, by immunocytochemical analyses. In some embodiments, mutation of any one of the energetically contributing residues of the target polypeptide (e.g., by alanine or homolog mutation, or by deletion or truncation) can disrupt the binding of the antibody such that the relative affinity ratio, $IC50_{(mutant\ target\ polypeptide)}/IC50_{(unmutated\ target\ polypeptide)}$, of the antibody may be greater than 1 (e.g., 2, 3, 4, 5, 10, 50, 100, 500, 1000 or greater).

The term "linker" as used herein refers to a chemical linking agent (e.g., homobifunctional and heterobifunctional cross-linkers (conjugation agents)) that may include a flexible arm, e.g., 2, 3, 4, 5, 6, 7, 8, 9, 10, 11, 12, 13, 14, or 15 carbon atoms, or one or more amino acids, that covalently link through peptide bonds, one molecule (e.g., an antibody of the invention) to another molecule (e.g., an agent, e.g., a diagnostic agent, e.g., a label, e.g., an ECL label or enzymatic label).

As used herein, the term "particulate demineralized bone matrix" refers to bone particles that have had some portion of their original mineral content removed by a demineralization process. Demineralization removes the inorganic mineral component of bone by employing acid solutions (see, e.g., Reddi et al. *Proc. Nat. Acad. Sci.* 69: 1601, 1972). The strength of the acid solution, the shape of the bone particles and the duration of the demineralization treatment can determine the extent of demineralization (see, e.g., Lewandrowski et al. *J Biomed Materials Res.* 31: 365, 1996).

The term "sample" is used to refer to any manufactured, processed, or biological sample. The sample can be silk sample, such as a cocoon, raw silk, processed silk (e.g., degummed silk or dissolved silk, e.g., lithium thiocyanate-dissolved silk), or synthetically generated silk.

The term "sericin" as used herein refers to a family of serine-rich silk proteins that coat silk fibroin threads and adhere the fibroin threads together. Sericin includes, for example, sericin protein from the silkworm *Bombyx mori* (UniProtKB/Swiss-Prot Identifier: P07856), which includes sericin isoforms 1B (UniProtKB/Swiss-Prot Identifier: P07856-1); 1A (UniProtKB/Swiss-Prot Identifier: P07856-2); and 1A' (UniProtKB/Swiss-Prot Identifier: P07856-3). Sericin isoform 1B, which is 1,186 amino acid residues in length, is used throughout as a reference sericin protein for all specified amino acid sequence or positional information.

By "silk" is meant a filamentous product secreted by a silkworm, such as the larva of the silk moth *Bombyx mori*, that contains both fibroin and sericin polypeptide components in its raw form.

A "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the subject is a human.

Indications that a composition, such as a silk sample, is "substantially free" of fibroin is mean that the composition comprises less than 5% fibroin by weight (e.g., less than 1%, less than 0.5%, less than 0.1%, less than 0.05%, less than 0.01%, or less than 0.005% fibroin by weight). Likewise, a composition, such as a silk sample, comprising less than 5% sericin by weight (e.g., less than 1%, less than 0.5%, less than 0.1%, less than 0.05%, less than 0.01%, or less than 0.005% sericin by weight) can be considered to be substantially free of sericin.

Other features and advantages of the invention will be apparent from the following detailed description and the claims.

II. Antibodies of the Invention

This invention features antibodies that bind to sericin, but not fibroin, polypeptides of silk. Accordingly, the antibodies bind to a polypeptide at an epitope in the amino acid sequence RSHHSGVNRLLHKPGQGKICLCFENIFDIPYHLRK (SEQ ID NO: 1), corresponding to residues 1148-1182 of sericin, which are not present in any fibroin sequence. For example, the epitope recognized by the antibodies may be in the amino acid sequence RSHHSGVNRLLHKPGQGK (SEQ ID NO: 2) or KICLCFENIFDIPYHLRK (SEQ ID NO: 3), corresponding to residues 1148-1165 and 1165-1182 of sericin, respectively. The antibodies may bind to a sericin polypeptide, such as sericin 1 or an isoform thereof that contains any one of SEQ ID NOs: 1-3.

A. Polyclonal Antibodies

In certain embodiments, the antibodies of the invention can also be polyclonal antibodies. Such polyclonal antibodies that bind to sericin but not fibroin can be generated, for example, in animals by multiple subcutaneous (sc) or intraperitoneal (ip) injections of a specific antigenic peptide sequence common to sericin polypeptides but absent in fibroin polypeptides, such as RSHHSGVNRLLHKPGQGKICLCFENIFDIPYHLRK (SEQ ID NO: 1), and an adjuvant. It can be useful to conjugate the antigenic peptide sequence to a protein that is immunogenic in the species to be immunized, e.g., keyhole limpet hemocyanin (KLH), serum albumin, bovine thyroglobulin, or soybean trypsin inhibitor using a bifunctional or derivatizing agent, for example, N-ethyl-(dimethylaminopropyl)carbodimide (EDC) (conjugation through the C-terminus of the antigenic peptide or by internal linkage to side chain carboxylic acids, as controlled by time and linker concentration), maleimide or maleimidobenzoyl sulfosuccinimide ester (conjugation through cysteine residues of the antigenic peptide), glutaraldehyde (conjugation through the N-terminus of the antigenic peptide), N-hydroxysuccinimide (conjugation through lysine residues), succinic anhydride, $SOCl_2$, or $R^1N=C=NR$, where R and $R^1$ are different alkyl groups.

Animals can be immunized against the antigenic peptide, or immunogenic conjugates or derivatives thereof (e.g., the antigenic peptide conjugated to KLH, a widely used carrier protein for generating a substantial immune response), by combining, for example, 1 mg or 1 µg of conjugate (for rabbits or mice, respectively) with 3 volumes of Freund's complete adjuvant and injecting the solution intradermally at multiple sites. One month later the animals can be boosted with ⅕ to ⅒ the original amount of conjugate in Freund's incomplete adjuvant by subcutaneous injection at multiple sites. 7 to 14 days later, the animals are bled and the serum is assayed for titer against the antigenic peptide. Animals can be boosted until the titer plateaus. Preferably, the animal is boosted with the conjugate, but conjugated to a different protein and/or through a different cross-linking agent. Conjugates also can be made in recombinant cell culture as protein fusions. Also, aggregating agents such as alum can be used to enhance the immune response. Methods for the production of polyclonal antibodies are described in numerous immunology textbooks, such as Davis et al. *Microbiology*, $3^{rd}$ *Edition*. Harper & Row, New York, N.Y., 1980.

B. Monoclonal Antibodies

In certain embodiments, the antibodies of the invention can also be monoclonal antibodies. Monoclonal antibodies can be prepared by recovering spleen cells from immunized animals (e.g., animals immunized with a specific antigenic peptide sequence common to sericin polypeptides but absent in fibroin polypeptides, such as RSHHSGVNRLLHKPGQGKICLCFENIFDIPYHLRK (SEQ ID NO: 1)) and immortalizing the cells in conventional fashion, for example, by fusion with myeloma cells or by Epstein-Barr virus transformation, and subsequent screening for clones expressing the desired antibody. See, for example, Kohler and Milstein *Eur. J. Immunol*. 6: 511, 1976. Monoclonal antibodies may alternatively be produced by recombinant methods.

C. Chimeric Antibodies

In certain embodiments, an antibody provided herein is a chimeric antibody. Certain chimeric antibodies are described, for example, in U.S. Pat. No. 4,816,567 and in Morrison et al., *Proc. Natl. Acad. Sci. USA*, 81: 6851-6855, 1984. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody.

D. Synthetic Antibodies

Antibodies of the invention can be produced by synthetic methods, such as by screening combinatorial libraries for antibodies with the desired activity or activities. For example, a variety of methods are known in the art for generating phage display libraries and screening such libraries for antibodies possessing the desired binding characteristics. Such methods are reviewed, for example, in Hoogenboom et al. in *Methods in Molecular Biology*. 178: 1-37, 2001 and further described, for example, in the McCafferty et al. *Nature* 348: 552-554, 1990; Clackson et al. *Nature*. 352: 624-628, 1991; Marks et al. *J. Mol. Biol*. 222: 581-597, 1992; Marks and Bradbury. *Methods in Molecular Biology* 248: 161-175, 2003; Sidhu et al. *J. Mol. Biol*. 338(2): 299-310, 2004; Lee et al. *J. Mol. Biol*. 340(5): 1073-1093, 2004; Fellouse. *Proc. Natl. Acad. Sci. USA* 101(34): 12467-12472, 2004; and Lee et al. *J. Immunol. Methods* 284(1-2): 119-132, 2004.

In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.*, 12: 433-455, 1994. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned to provide a single source of antibodies to a wide range of non-self and also self antigens without any immunization as described by Griffiths et al., *EMBO J*. 12: 725-734, 1993. Finally, naive libraries can also be made synthetically by cloning un-rearranged V-gene segments from stem cells and using PCR primers containing random sequence to encode the highly variable CDR3 regions and to accomplish rearrangement in vitro, as described by Hoogenboom and Winter. *J. Mol. Biol.*, 227: 381-388, 1992. Patents and patent publications describing antibody phage libraries include, for example, U.S. Pat. Nos. 5,750,373, 7,985,840, 7,785,903, and 8,054,268, and U.S. Patent Publication Nos. 2005/0079574, 2007/0117126, 2007/0160598, 2007/0237764, and 2007/0292936.

E. Multispecific Antibodies

In certain embodiments, an antibody provided herein is a multispecific antibody, such as a bispecific antibody. Multispecific antibodies can be monoclonal antibodies that have binding specificities for at least two different sites. In certain embodiments, one of the binding specificities is for sericin and the other is for a different target polypeptide. In certain embodiments, bispecific antibodies may bind to two different epitopes of sericin (e.g., one epitope within residues 1148-1182 of sericin (SEQ ID NO: 1) and another epitope within residues 1-1147 of sericin (SEQ ID NO: 4) or residues 1182-1186 of sericin (SEQ ID NO: 5)). Bispecific antibodies can be prepared as full length antibodies or antibody fragments.

Techniques for making multispecific antibodies include, but are not limited to, recombinant co-expression of two immunoglobulin heavy chain-light chain pairs having different specificities (see, e.g., Milstein and Cuello. *Nature*. 305: 537, 1983; WO 93/08829; and Traunecker et al. *EMBO J*. 10: 3655, 1991) and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980 and Brennan et al. *Science*. 229: 81, 1985); using leucine zippers to produce bispecific antibodies (see, e.g., Kostelny et al. *J. Immunol*. 148(5): 1547-1553, 1992); using "diabody" technology for making bispecific antibody fragments (see, e.g., Hollinger et al. *Proc. Natl. Acad. Sci. USA*. 90: 6444-6448, 1993); and using single-chain Fv (sFv) dimers (see, e.g., Gruber et al. *J. Immunol*. 152: 5368, 1994).

F. Antibody Fragments

In certain embodiments, any one of the antibodies provided herein can be an antibody fragment. Antibody fragments include, but are not limited to, Fab, Fab', Fab'-SH, F(ab')$_2$, Fv, and scFv fragments, and other fragments described below. For a review of certain antibody fragments, see, for example, Hudson et al. *Nat. Med*. 9: 129-134, 2003. For a review of scFv fragments, see, for example, Pluckthun in *The Pharmacology of Monoclonal Antibodies*, Vol. 113, Rosenburg and Moore Eds., (Springer-Verlag, New York), pp. 269-315, 1994; WO 93/16185; and U.S. Pat. Nos. 5,571,894 and 5,587,458. For discussion of Fab and F(ab')$_2$ fragments comprising salvage receptor binding epitope residues and having increased in vivo half-life, see, for example, U.S. Pat. No. 5,869,046.

Diabodies are antibody fragments with two antigen-binding sites that may be bivalent or bispecific. See, for example, EP 404,097; WO 1993/01161; Hudson et al. *Nat. Med*. 9: 129-134, 2003; and Hollinger et al. *Proc. Natl. Acad. Sci. USA* 90: 6444-6448, 1993. Triabodies and tetrabodies are also described in Hudson et al. *Nat. Med*. 9: 129-134, 2003.

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody, as well as production by recombinant host cells (e.g., *E. coli* or phage), as described herein.

G. Antibody Variants

In certain embodiments, amino acid sequence variants of the antibodies or antibody fragments provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

In certain embodiments, antibody variants having one or more (e.g., 1, 2, or 3 or more) amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved target polypeptide (e.g., sericin) binding.

TABLE 1

Preferred and Exemplary Amino Acid Substitutions

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

H. Antibody Conjugates

In some embodiments, the antibodies of the invention may be a conjugate (i.e., a conjugated antibody), which further includes one or more agents (e.g., 1, 2, 3, or 4 or more agents), such as diagnostic agents. The diagnostic agent, for example, can be a label, such as an electrochemiluminescent (ECL) label, enzymatic label, fluorescent label, or radiolabel.

The ECL label may, for example, be a Sulfo-TAG label (Meso Scale Discovery), which is an amine-reactive, N-hydroxysuccinimide ester which readily couples to primary amine groups under mildly basic conditions to form a stable amide bond, and which has the structure:

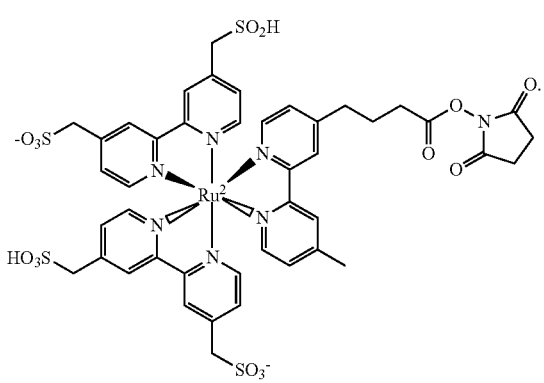

The enzymatic label may, for example, be horseradish peroxidase (HRP), which decomposes two molecules of hydrogen peroxide, the natural substrate, into water and oxygen. HRP initiates this reaction when it donates a pair of electrons to hydrogen peroxide. The enzyme subsequently extracts electrons (oxidizes) from a suitable donor. Some electron donors become activated upon the loss of electrons and may react with each other to form a polymer which precipitates. A donor that forms an intensely colored precipitate upon release of electrons (oxidation) can be a good HRP substrate for an immunological detection system. The low specificity of HRP for the electron donor has allowed the development of many chromogenic substrates for HRP, such as, for example, 3,3',5,5'-tetramethylbenzidine ("TMB"), 4-chloro-1-naphthol ("4CN"), 3-amino-9-ethyl-carbazole ("AEC"), 3,3'-diaminobenzidine ("DAB"), and their derivatives. U.S. Pat. No. 4,503,143 and WO 91/06672 describe the use of TMB and its derivatives as chromogenic substances for detection of antigen or antibody in colorimetric enzyme immunoassays.

The fluorescent label may, for example, be xanthene derivatives (e.g., fluorescein, rhodamine, eosin, Texas red); coumarin and its derivatives; cyanine and its derivatives (e.g., indocarbocyanine, oxacarbocyanine, thiacarbocyanine, and merocyanine); green fluorescent protein (GFP) and its variants (e.g., yellow fluorescent protein (YFP) and red fluorescent protein (RFP)); oxadiazole and its derivatives (e.g., pyridyloxazole, nitrobenzoxadiazole, and benzoxadiazole); anthracene and its derivatives (e.g., anthraquinones); oxazine and its derivatives (e.g., Nile red, Nile blue, cresyl violet); acridine and its derivatives (e.g., proflavin); and tetrapyrrole and its derivatives (e.g., phthalocyanine, and bilirubin).

The radiolabel may, for example, include a radioactive atom for scintigraphic studies, for example $Tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The one or more (e.g., 1, 2, or 3 or more) agents (e.g., diagnostic agents) may be directly conjugated to an antibody of the invention (e.g., by way of a direct covalent or non-covalent interaction). An agent may be directly conjugated to an antibody of the invention, for example, by a direct peptide bond. In other instances, the direct conjugation is by way of a direct non-covalent interaction, such as an interaction between an antibody of the invention and an agent that specifically binds to the antibody.

The conjugation of an agent (e.g., a diagnostic agent), including enzymatic labels (e.g., HRP), to an antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in *Methods in Enzymology*, ed. J. J. Langone and H. Van Vunakis, Vol. 73, Academic Press, New York, N.Y., pp. 147-166, 1981.

The one or more (e.g., 1, 2, or 3 or more) agents (e.g., diagnostic agents) may be indirectly conjugated to an antibody or other polypeptide of the invention (e.g., by way of a linker with direct covalent or non-covalent interactions). Linkers can be chemical linking agents, such as homobifunctional and heterobifunctional cross-linkers, which are available from many commercial sources. Regions available for cross-linking may be found on the antibodies of the present invention. The linker may comprise a flexible arm, e.g., 2, 3, 4, 5, 6, 7, 8, 9, 10, 11, 12, 13, 14, or 15 carbon atoms. Exemplary linkers include BS3 ([Bis(sulfosuccinimidyl)suberate]; BS3 is a homobifunctional N-hydroxysuccinimide ester that targets accessible primary amines), NHS/EDC (N-hydroxysuccinimide and N-ethyl-(dimethylaminopropyl)carbodiimide; NHS/EDC allows for the conjugation of primary amine groups with carboxyl groups), sulfo-EMCS ([N-e-Maleimidocaproic acid]hydrazide; sulfo-EMCS are heterobifunctional reactive groups (maleimide and NHS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups).

To form covalent bonds, one can use as a chemically reactive group a wide variety of active carboxyl groups (e.g., esters) where the hydroxyl moiety is physiologically acceptable at the levels required to modify the peptide. Particular agents include N-hydroxysuccinimide (NHS), N-hydroxysulfosuccinimide (sulfo-NHS), maleimide-benzoyl-succinimide (MBS), gamma-maleimido-butyryloxy succinimide ester (GMBS), maleimido propionic acid (MPA) maleimido hexanoic acid (MHA), and maleimido undecanoic acid (MUA).

Primary amines are the principal targets for NHS esters. Accessible α-amino groups present on the N-termini of proteins and the ε-amine of lysine react with NHS esters. An amide bond is formed when the NHS ester conjugation reaction reacts with primary amines releasing N-hydroxysuccinimide. These succinimide containing reactive groups are herein referred to as succinimidyl groups. In certain embodiments of the invention, the functional group on the antibody will be a thiol group and the chemically reactive group will be a maleimido-containing group such as gamma-maleimide-butrylamide (GMBA or MPA). Such maleimide containing groups are referred to herein as maleido groups.

The maleimido group is most selective for sulfhydryl groups on peptides when the pH of the reaction mixture is 6.5-7.4. At pH 7.0, the rate of reaction of maleimido groups with sulfhydryls (e.g., thiol groups on proteins such as serum albumin or IgG) is 1000-fold faster than with amines. Thus, a stable thioether linkage between the maleimido group and the sulfhydryl can be formed.

In other embodiments, the linker includes at least one amino acid (e.g., a peptide of at least 2, 3, 4, 5, 6, 7, 10, 15, 20, 25, 40, or 50 amino acids). In certain embodiments, the linker is a single amino acid (e.g., any naturally occurring amino acid such as Cys). In other embodiments, a glycine-rich peptide such as a peptide can be used, as described in U.S. Pat. No. 7,271,149. In other embodiments, a serine-rich peptide linker can be used, as described in U.S. Pat. No. 5,525,491. In some cases, the linker can be a single amino acid (e.g., any amino acid, such as Gly or Cys).

Examples of suitable linkers are succinic acid, Lys, Glu, and Asp, or a dipeptide such as Gly-Lys. When the linker is succinic acid, one carboxyl group thereof may form an amide bond with an amino group of the amino acid residue, and the other carboxyl group thereof may, for example, form an amide bond with an amino group of the peptide or substituent. When the linker is Lys, Glu, or Asp, the carboxyl group thereof may form an amide bond with an amino group of the amino acid residue, and the amino group thereof may, for example, form an amide bond with a carboxyl group of the substituent. When Lys is used as the linker, a further linker may be inserted between the ε-amino group of Lys and the substituent. In one particular embodiment, the further linker is succinic acid which, e.g., forms an amide bond with the ε-amino group of Lys and with an amino group present in the substituent. In one embodiment, the further linker is Glu or Asp (e.g., which forms an amide bond with the ε-amino group of Lys and another amide bond with a carboxyl group present in the substituent), that is, the substituent is a $N^\epsilon$-acylated lysine residue.

III. Methods for Selectively Detecting Sericin

The invention features methods for selectively detecting sericin in a sample using, for example, an antibody of the invention as a capture antibody, which binds to sericin at an epitope within residues 1148-1182 of sericin (SEQ ID NO: 1). In one aspect, the method includes the steps of: (a) immobilizing the sample to a solid support to form an immobilized sample; (b) contacting the immobilized sample with a capture antibody to form an immobilized sericin-capture antibody complex, wherein the capture antibody binds to sericin at an epitope within residues 1148-1182 of sericin (SEQ ID NO: 1); (c) separating unbound capture antibody from the immobilized sericin-capture antibody complex; and (d) measuring the level of sericin bound to the capture antibody using a detection means for the capture antibody. In one embodiment, the capture antibody is directly detectable.

In another aspect, the method for selectively detecting sericin in a sample comprises the steps of: (a) immobilizing the sample to a solid support to form an immobilized sample; (b) contacting the immobilized sample with a capture antibody to form an immobilized sericin-capture antibody complex, wherein the capture antibody binds to sericin at an epitope within residues 1148-1182 of sericin (SEQ ID NO: 1); (c) separating unbound capture antibody from the immobilized sericin-capture antibody complex; (d) contacting the immobilized sericin-capture antibody complex with a detectable antibody that binds the capture antibody to form an immobilized sericin-capture antibody-detectable antibody complex; (e) separating unbound detectable antibody from the immobilized sericin-capture antibody-detectable antibody complex; and (f) measuring the level of sericin bound to the capture antibody using a detection means for the detectable antibody. In one embodiment, the detectable antibody is directly detectable.

In another aspect, the method for selectively detecting sericin in a sample comprises the steps of: (a) immobilizing a capture antibody to a solid support to form an immobilized capture antibody, wherein the capture antibody binds to sericin at an epitope within residues 1148-1182 of sericin (SEQ ID NO: 1); (b) contacting the immobilized capture antibody with the sample to form an immobilized capture antibody-sericin complex; (c) separating unbound sample from the immobilized capture antibody-sericin complex; (d) contacting the immobilized capture antibody-sericin complex with a detectable antibody that binds to sericin at an epitope within residues 1-1147 of sericin (SEQ ID NO: 4) or residues 1182-1186 of sericin (SEQ ID NO: 5) to form an immobilized capture antibody-sericin-detectable antibody complex; (e) separating unbound detectable antibody from the immobilized capture antibody-sericin-detectable antibody complex; and (f) measuring the level of sericin bound to the capture antibody using a detection means for the detectable antibody. In one embodiment, the detectable antibody is directly detectable.

In any one of the above methods, the sample can be a silk sample (e.g., a dissolved silk sample, e.g., a lithium thiocyanate-dissolved silk sample).

The solid support can be any inert support or carrier that is essentially water insoluble and useful in immunometric assays. The solid support can be selected from any shape, form, and size (e.g., sheets, plates, test particles (e.g., beads and microspheres), test tubes, test sticks, test strips, porous matrices, wells, or assay plates (e.g., ELISA plates, microtiter/microwell plates). Examples of commonly used supports include small sheets, Sephadex, polyvinyl chloride, plastic beads, and assay plates (e.g., microtiter plates) or test tubes including polyethylene, polypropylene, or polystyrene. In one embodiment, the solid support is a microtiter plate, for example, a microtiter plate including polystyrene. Also common are particulate materials, such as filter paper, agarose, cross-linked dextran, and other polysaccharides.

For methods requiring the immobilization of the capture antibody to the solid surface, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are suitably employed. In such embodiments, the capture antibody may be linked by a non-covalent or covalent interaction or physical linkage as desired. Techniques for attachment include those described in U.S. Pat. No. 4,376,110 and the references cited therein. For covalent interactions or physical linkage, the microtiter plate or other solid phase can be incubated with a cross-linking agent together with the capture antibody under conditions well known in the art, for example, such as for 1 hour at room temperature. Commonly used cross-linking agents for attaching the capture antibody to the solid support substrate include, for example, 1,1-bis(diazoacetyl)-2-phenylethane, glutaraldehyde, N-hydroxysuccinimide esters, for example, esters with 4-azido-salicylic acid, homobifunctional imidoesters, including disuccinimidyl esters such as 3,3'-dithiobis-(succinimidyl-propionate), and bifunctional maleimides such as bis-N-maleimido-1,8-octane. Derivatizing agents such as methyl-3-[(p-azidophenyl)-dithio]pro-pioimi-date yield photoactivatable intermediates capable of forming cross-links in the presence of light.

In certain embodiments, the sericin detection methods of the invention may have a sensitivity for sericin of ≤100 ng/ml (e.g., ≤50 ng/ml, ≤10 ng/ml, ≤5 ng/ml, ≤1 ng/ml, ≤0.1 ng/ml, ≤0.01 ng/ml, or ≤0.001 ng/ml). For example, the sericin detection methods of the invention may have a sensitivity for sericin of ≤1 ng/ml.

In certain embodiments, the sericin detection methods of the invention may have a detection limit for sericin of ≤5% (e.g., ≤1%, ≤0.5%, ≤0.1%, ≤0.05%, ≤0.01%, ≤0.005%, ≤0.00125%, or ≤0.001%). In some embodiments, the detection limit for sericin is ≤1%. In some embodiments, the detection limit for sericin is ≤0.00125% (i.e., the sericin detection method is capable of detecting a sericin content (e.g., in silk) of 0.00125%).

IV. Immunoassay Kits for Selectively Detecting Sericin

As a matter of convenience, the sericin detection methods of this invention can be provided in the form of a kit (e.g., an immunoassay kit). Such a kit for selectively detecting sericin in a sample (e.g., a silk sample) is a packaged combination including the basic elements of (a) a capture antibody that binds to sericin at an epitope within residues 1148-1182 of sericin (SEQ ID NO: 1); and (b) a solid support (e.g., a microtiter plate).

In some embodiments, the sample is immobilized on the solid support. The sample can be immobilized on the solid support (e.g., on wells within a microtiter plate), for example, by adsorption onto a protein-binding surface (e.g., polystyrene). When the sample is immobilized on the solid support, the kit can be useful, for example, for both the sericin ECL-based assay and the sericin antigen-down ELISA described herein. A kit useful for ECL-based sericin detection, for example, may include a detectable capture antibody that binds to sericin at an epitope within residues 1148-1182 of sericin (SEQ ID NO: 1). The detectable capture antibody may be directly detectable, for example, by an ECL label, such as a Sulfo-TAG label. A kit useful for antigen-down ELISA-based sericin detection, however, may further include a detectable antibody that binds the capture antibody. Although both the detectable antibody and the capture antibody can be detectable (e.g., directly detectable), the capture antibody need not be so, and, in fact, may not be conjugated to any agent.

In some embodiments, the capture antibody is immobilized to the solid support of the kit. When the capture antibody is immobilized to the solid support, the kit can be useful, for example, for the sandwich ELISA described herein. A kit useful for the sandwich ELISA may, for example, further include a detectable antibody that binds to at least one spatially distinct antigenic epitope of sericin (e.g., an epitope within residues 1-1147 of sericin (SEQ ID NO: 4) or residues 1182-1186 of sericin (SEQ ID NO: 5)). In some embodiments, the detectable antibody is directly detectable. The detectable antibody, for example, may be conjugated to an agent, such as a diagnostic label. The diagnostic label can be an ECL label, an enzymatic label, a fluorescent label, or a radiolabel. For example, the detectable antibody can be conjugated (directly or indirectly) to an enzymatic label, such as an HRP label or alkaline phosphatase (AP) label.

In some embodiments, the immunoassay kits of the invention may have a sensitivity for sericin of ≤100 ng/ml (e.g., ≤50 ng/ml, ≤10 ng/ml, ≤5 ng/ml, ≤1 ng/ml, ≤0.1 ng/ml, ≤0.01 ng/ml, or ≤0.001 ng/ml). For example, the immunoassay kits of the invention may have a sensitivity for sericin of ≤1 ng/ml.

In some embodiments, the immunoassay kits of the invention may have a detection limit for sericin of ≤5% (e.g., ≤1%, ≤0.5%, ≤0.1%, ≤0.05%, ≤0.01%, ≤0.005%, ≤0.00125%, or ≤0.001%). In some embodiments, the detection limit for sericin is ≤1%. In some embodiments, the detection limit for sericin is ≤0.00125% (i.e., the immunoassay is capable of detecting a sericin content (e.g., in silk) of 0.00125%).

In certain embodiments, the kit can contain multiple ELISAs for comparison studies. In addition, the kit may also contain instructions for carrying out the assay and/or a sericin as an antigen standard (e.g., sericin peptide, which may be recombinantly produced or synthesized, or sericin substantially free of fibroin, such as a sericin fraction obtained from degumming/washing silk), as well as other additives such as stabilizers, washing and incubation buffers, and the like.

The components of the kit will be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

V. Methods for Validating Silk

The sericin detection methods and/or immunoassay kits of the invention can be useful in validating whether a silk sample is suitable for a particular use (e.g., medical, research, cosmetic, or textile use) based on measured sericin content. The silk sample may be a batch of raw, treated/washed (e.g., alkaline-washed silk, e.g., sodium carbonate-washed), or genetically engineered silk.

Accordingly, methods of the invention include determining whether a batch of silk is suitable for medical use, the method including the steps of (a) providing a batch of silk, wherein the silk has a sericin content measured using one or more (e.g., 1, 2, or 3 or more) of the detection methods and/or immunoassay kits of the invention, and (b) on the basis of the sericin content, determining whether the batch of silk is suitable for medical use. As sericin is known to be antigenic and capable of eliciting a strong immune, allergic, or hyper-T-cell type (versus the normal mild "foreign body" response) response, the batch of silk can be determined as suitable for medical use if it is biocompatible and, for example, contains a low sericin content, such as ≤0.5% sericin by weight (e.g., ≤0.1%, ≤0.05%, ≤0.01%, or ≤0.00125% sericin by weight), as measured using one or more (e.g., 1, 2, or 3 or more) of the detection methods and/or immunoassay kits of the invention. In certain embodiments, the methods include determining whether a batch of silk is suitable for use as reinforcing fillers in a scaffold for tissue engineering and/or bone repair (see, e.g., PCT Publication Nos. WO 2013/096797 and WO 2013/152265).

In other embodiments, the methods of the invention include determining whether a batch of silk is suitable for cosmetic use (e.g., use in a skin care, hair care, or hair coloring composition), the method including the steps of (a) providing a batch of silk, wherein the silk has a sericin content measured using one or more (e.g., 1, 2, or 3 or more) of the detection methods and/or immunoassay kits of the invention, and (b) on the basis of the sericin content, determining whether the batch of silk is suitable for cosmetic use (e.g., use in the skin care, hair care, or hair coloring composition). For example, the batch of silk can be determined as suitable for use in a hair care composition (e.g., shampoo or conditioner) or skin care composition (e.g., skin lotion, cream, ointment, or salve) if the batch of silk contains a high sericin and low fibroin content (e.g., silk that is substantially free of fibroin). See, e.g., Padamwar et al. *J. Sci. & Indust. Res.* 63: 323-329, 2004 for other specific applications of sericin.

VI. Methods for Cryoprotecting Cells

Cryopreservation is a pivotal process in cellular engineering for creating a continuous source of generated functional cell lines and for the convenience of various medical treatments that involve cell culture. Fetal bovine serum (FBS) supplemented with 10% (v/v) DMSO is extensively used as a freezing medium, for example, for mammalian cells, but the use of such a freezing medium poses concerns regarding BSE (bovine spongiform encephalopathy) and other infections such as viruses. It has therefore been established that silk sericin, in particular, can be used as an alternative to FBS in a freezing media (see, e.g., Sasaki et al. *Biotech. Appl. Biochem.* 42: 183-188, 2005).

Accordingly, in a related aspect, the invention features methods for cryoprotecting cells, the method including the steps of (a) providing a serum-free freezing medium, the serum-free freezing medium including sericin and substantially free of fibroin as measured using one or more (e.g., 1, 2, or 3 or more) of the detection methods and/or immunoassay kits of the invention; (b) resuspending the cells with the serum-free freezing medium in a cryovial; and (c) freezing the cryovial. In some embodiments, the cells are eukaryotic cells (e.g., mammalian cells). In other embodiments, the cells are prokaryotic cells (e.g., *E. coli* cells).

VII. Methods for Medical Use

The invention also features methods for inserting a composition including silk into a subject (e.g., for the treatment of bone defects). The incorporation of silk fibers into the composition results in a composition that is mechanically strengthened and reinforced such that aggressive manipulation of the composition by a physician during the implantation procedure would occur without tearing or puncturing. As silk sericin can elicit an unwanted immune response, great care should be given to implant or insert only compositions that contain silk with biocompatible sericin levels.

Thus, the invention features methods for inserting an implantable composition comprising silk into a subject, the method including (a) providing silk fibers, wherein the silk fibers have a sericin content of ≤0.5% (w/w) (e.g., ≤0.1%, ≤0.05%, ≤0.01%, or ≤0.00125% sericin (w/w)) measured using one or more (e.g., 1, 2, or 3 or more) of the detection methods and/or immunoassay kits of the invention; (b) incorporating the silk fibers into the implantable composition; and (c) inserting the implantable composition into the subject. The invention also features methods for inserting an implantable composition comprising silk into a subject, the method including (a) providing an implantable composition comprising silk, wherein the silk has a sericin content of ≤0.5% (w/w) (e.g., ≤0.1%, ≤0.05%, ≤0.01%, or ≤0.00125% sericin (w/w)) measured using; and (b) inserting the implantable composition into the subject.

In a related aspect, the invention features methods for implanting a pliable implantable composition into a subject, the pliable implantable composition comprising: (a) from 5% to 20% (w/w) (e.g., 5% to 10%, 10% to 15%, or 15% to 20% (w/w)) a dispersing agent selected from glycerin, polyethylene glycol, N-methyl pyrrolidone, and triacetin; (b) from 1.0% to 6.0% (w/w) (e.g., 1.0% to 1.5%, 1.5% to 2.5%, 2.5% to 4.5%, or 3.5% to 6.0% (w/w)) a polymer selected from sodium carboxymethylcellulose, polyvinylalcohol, hydroxyethyl cellulose, hydroxypropyl methylcellulose, methylcellulose, ethylcellulose, and hyaluronic acid; (c) from 65% to 90% (w/w) (e.g., 65% to 75%, 75% to 85%, 80% to 90%, or 85% to 90% (w/w)) particulate bone graft substitute or particulate demineralized bone matrix having a mean particle size of from 100 μm to 1000 μm (e.g., 150±50, 250±50, 350±50, 450±50, 550±50 μm, 600±50 μm, or 750±250 μm); and (d) from 0.2% to 3.5% (w/w) (e.g., 0.2% to 0.6%, 0.5% to 0.9%, 0.8% to 1.2%, 1.1% to 2.0%, 1.5% to 2.2%, 1.9% to 2.7%, or 2.4% to 3.5% (w/w)) silk fibers having a sericin content of ≤0.5% (w/w) (e.g., ≤0.1%, ≤0.05%, ≤0.01%, or ≤0.00125% sericin (w/w)) measured using one or more (e.g., 1, 2, or 3 or more) of the above methods and/or immunoassay kits of the invention, wherein the method comprises inserting the pliable implantable composition into the subject at an osteogenic site. In some embodiments, the silk fibers have an average length of from 0.5 to 15 mm (e.g., 0.5 to 1.5 mm, 1.0 to 3.0 mm, 2.5 to 15 mm, 4.5 to 9 mm, 7.0 to 15 mm, or 10 to 15 mm).

The bone graft substitute can be a particulate ceramic, for example, selected from calcium phosphate materials, such as mineralized bone matrix, deorganified bone mineral/anorganic bone mineral, or a mixture thereof. The calcium phosphate may be any biocompatible, calcium phosphate material known in the art. The calcium phosphate material may be produced by any one of a variety of methods and using any suitable starting components. For example, the calcium phosphate material may include amorphous, apatitic calcium phosphate. Calcium phosphate material may be produced by solid-state acid-base reaction of crystalline calcium phosphate reactants to form crystalline hydroxyapatite solids. Other methods of making calcium phosphate materials are known in the art, some of which are described below. Alternatively, the calcium phosphate material can be crystalline hydroxyapatite (HA). Crystalline HA is described, for example, in U.S. Pat. Nos. Re. 33,221 and Re. 33,161. These patents teach preparation of calcium phosphate remineralization compositions and of a finely crystalline, non-ceramic, gradually resorbable hydroxyapatite carrier material based on the same calcium phosphate composition. A similar calcium phosphate system, which consists of tetracalcium phosphate (TTCP) and monocalcium phosphate (MCP) or its monohydrate form (MCPM), is described in U.S. Pat. Nos. 5,053,212 and 5,129,905. This calcium phosphate material is produced by solid-state acid-base reaction of crystalline calcium phosphate reactants to form crystalline hydroxyapatite solids. Carbonate substituted crystalline HA materials (commonly referred to as dahllite) may be prepared (see U.S. Pat. No. 5,962,028). These HA materials (commonly referred to as carbonated hydroxyapatite) can be formed by combining the reactants with an aqueous liquid to provide a substantially uniform mixture, shaping the mixture as appropriate, and allowing the mixture to harden in the presence of water. During hardening, the mixture crystallizes into a solid and essentially monolithic apatitic structure. The reactants will generally include a phosphate source, e.g., phosphoric acid or phosphate salts, an alkali earth metal, particularly calcium, optionally crystalline nuclei, particularly hydroxyapatite or calcium phosphate crystals, calcium carbonate, and a physiologically acceptable lubricant. The dry ingredients may be pre-prepared as a mixture and subsequently combined with aqueous liquid ingredients under conditions in which substantially uniform mixing occurs.

The above silk-containing compositions may be prepared, implanted, or administered as described, for example, in PCT Publication No. WO 2013/096797.

For any of the above methods, the subject may, for example, be a human subject.

EXAMPLES

The following examples are provided to illustrate, but not to limit the presently claimed invention.

Example 1. Materials and Methods

Preparation of Sericin Standard

This procedure was designed to generate a pure sericin preparation, contaminated with as little fibroin as possible. To this end, 150 mg of diced cocoon were measured and placed in a Wheaton glass vial. 10 ml 8M urea was added. The vial was placed in a dry bath and heated to 80° C. for 30 minutes. The vial was then removed from the heat and allowed to cool. The urea solution containing the sericin was decanted into a 50-ml polypropylene tube. It was then centrifuged at 4200 rpm for 10 minutes to remove solids. The liquid was decanted and the sericin precipitated by adding ethanol to 75%. The sericin pellet was washed twice with 80% ethanol to remove residual urea. The sericin pellet was dried overnight in a lyophilizer. The dried sericin pellet was massed and resuspended to 10 mg/ml in 9M lithium bromide. In order to generate sufficient sericin, 18 150-mg quantities of cocoon, as described above, were processed. Solutions were pooled as appropriate.

Dissolution of Silk Protein in LiSCN (with or without 2% BME)

Saturated LiSCN was prepared by mixing 100 grams of LiSCN with 40 ml of water. 200 mg cocoon or silk were measured and placed in a 15-ml polypropylene tube. Cocoons were cut into small pieces (approximately 4 mm×4 mm) before placing in the tube. 10 ml of saturated LiSCN were added (with or without 2% beta-mercaptoethanol (BME)). The mix was rotated end-over-end overnight at room temperature.

Extraction of Sericin with 8M Urea using a Dry Bath

Extraction of cocoons or silk with 8M urea is reported to remove most, if not all, sericin (Takasu et al. *Biosci. Biotechnol. Biochem.* 12: 2715-2718, 2002; Wray et al. *J. Biomed. Mater.* 99: 89-101, 2011). 100 mg cocoon (dried) or silk were measured and placed in a Wheaton glass vial. 10 ml of 8M urea was added. The vial was placed in a dry bath and heated to 85° C. for 30 minutes. The vial was removed from the heat and allowed to cool. The urea solution containing sericin was then decanted.

Example 2. Anti-Sericin Peptide Polyclonal Antibodies

A peptide sequence common to a number of sericin species but not present in any fibroin sequence was identified (SEQ ID NO: 1). Two 18-amino acid peptide sequences were generated based on their antigenicity, presence in three published sericin sequences (see, e.g., Takasu et al. *Bioscience, Biotechnology, and Biochemistry.* 66(12): 2715-2718, 2002), and absence from the published fibroin sequence (see, e.g., UniProtKB/Swiss-Prot Identifiers: P05790 and P21828). The sequences of the two proposed peptides are provided in Table 2. The two peptides were used to immunize a total of four rabbits, two rabbits with each peptide, following their conjugation to the carrier, KLH, via either EDC and glutaraldehyde (for the peptide of SEQ ID NO: 2) or maleimide, EDC, and glutaraldehyde (for the peptide of SEQ ID NO: 3). Antibody titers for each rabbit are also provided in Table 2.

TABLE 2

Immunogenic Sericin Peptides and Antibody Titers

| Peptide | Sequence | Rabbit | Titer (Day 72) |
|---|---|---|---|
| Ser1-1148-1165 | RSHHSGVNRLLHKPGQGK (SEQ ID NO: 2) | PA6632 | 102,400 |
|  |  | PA6633 | 25,600 |
| Ser1-1165-1182 | KICLCFENIFDIPYHLRK (SEQ ID NO: 3) | PA6634 | 12,800 |
|  |  | PA6635 | 25,600 |

The antibodies were numbered "33" through "35," a shortening of the animal number from which they were generated. Initial studies revealed that Antibodies 32, 34, and 35 worked well when used in an ELISA-based assay, but Antibody 33 did not. A proportion of Antibodies 32 and 35 were affinity purified by conventional means. The titer of Antibody 35 was low to begin with and, unfortunately, the affinity purification produced very little purified Antibody 35. The purified Antibodies 32 and 35 were subsequently conjugated with diagnostic labels (e.g., Sulfo-TAG and horseradish peroxidase (HRP) labels) according to manufacturer's instructions, as needed, for the sericin ECL-based assay and ELISAs described below.

Example 3. ECL-Based Sericin Assay

All ECL-based assay steps were performed at room temperature and all reagents were allowed to reach room temperature prior to use. The ECL-based sericin assay requires several sequential changes of reagents. Each change of reagent was accomplished by carefully inverting the microtiter plate over a sink to remove the bulk of the spent reagent. The inverted plate was then tapped on a paper towel to remove any remaining liquid.

The required wells of an MSD 96-well standard bind microtiter plate (Meso Scale Discovery (MSD), Cat. No. L11XA-3) were loaded with 100 μl of sericin standard preparation, sericin peptide, or sericin sample diluted in PBS using a micropipette. The microtiter plate was covered with an adhesive seal and incubated for 3 hours with shaking. The sericin solution(s) were discarded. Each well of the microtiter plate was rinsed by filling each well with 150 μl Wash Solution (PBS containing 0.05% Tween 20) with a micropipette and discarding. This was repeated twice for a total of three rinses. Each well of the microtiter plate was loaded with 150 μl Blocking Solution (PBS containing 1% BSA) using a micropipette. The microtiter plate was allowed to incubate for 30 min with shaking. The Blocking Solution was discarded, and each well of the microtiter plate was washed as above. The microtiter plate wells were accurately loaded with 110 μl SulfoTAG-labeled anti-sericin antibody diluted 1:1000 in Antibody Dilution Buffer (PBS containing 1% BSA and 0.05% Tween 20; ADB) using a micropipette. The microtiter plate was covered with an adhesive seal and incubated overnight with shaking. The sericin antibody solution was discarded, and each well of the microtiter plate was rinsed as above. Each well was accurately loaded with 100 μl MSD Read Buffer T (2x) using a micropipette, prepared by mixing equal volumes of MSD Read Buffer T (4x) and water. The ECL signal of each well was read using the MSD SECTOR Imager 2400A, and the raw data were analyzed.

Figure 2:
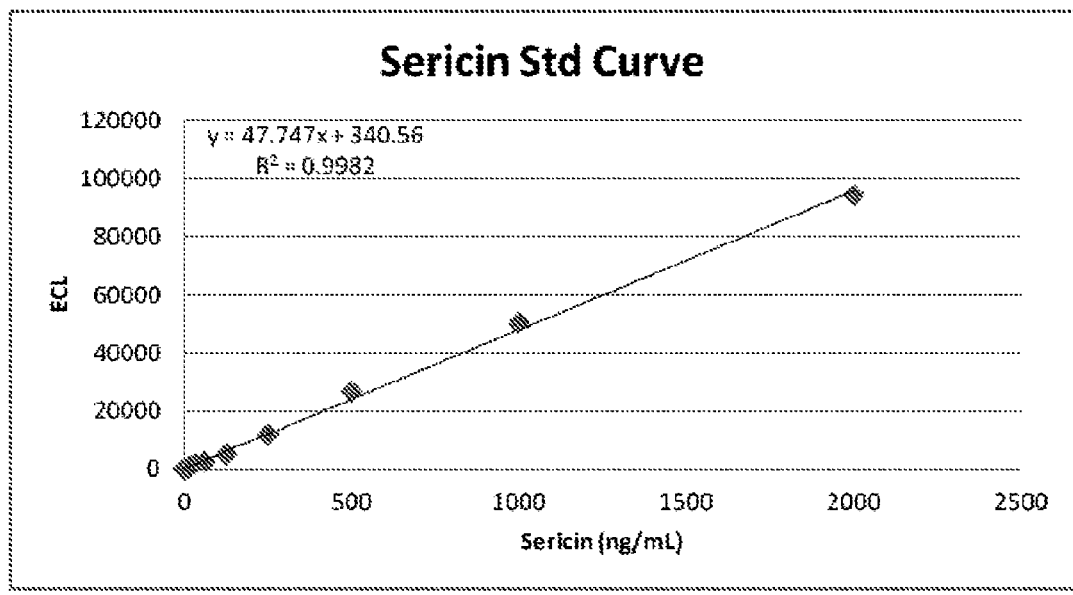
FIG. 2 is a graph showing an extended sericin standard curve for the ECL-based sericin assay, indicating that the ECL-based assay exhibits a linear range of detection of at least 0 to 2000 ng/ml, with an $R^2$ value of 0.9982.

If performed under the optimal conditions described above, the ECL-based sericin assay provides a sensitivity for sericin of greater than 1 ng/mL and exhibits a linear range of detection of at least 0 to 2000 ng/ml with an $R^2$ value of 0.99 (FIGS. 1 and 2). The ECL-based sericin assay was used to measure the sericin content of raw and washed silk obtained from Ashland Bay, Inc. (Wilsonville, Oreg.). Sericin was measured both in urea extracts and in LiSCN-dissolved silk, and the results are set forth in below in Tables 3 and 4, respectively. To provide values for assay precision, each sericin sample (dissolved or extracted) was prepared three separate times and the first sample was assayed five separate times by the ECL method. Each ELC-based measurement was made in quadruplicate.

TABLE 3

ECL-Based Measurements of Sericin Content in Urea Extracts

| Silk | Sample | Repeat | Dilution | Sericin Content (%) |
|------|--------|--------|----------|---------------------|
| Raw  | 1      | 1      | 20K      | 1.5                 |
|      |        |        | 80K      | 1.3                 |
|      |        | 2      | 20K      | 1.4                 |
|      |        |        | 80K      |                     |
|      |        | 3      | 20K      | 1.4                 |
|      |        |        | 80K      |                     |
|      |        | 4      | 20K      | 1.6                 |
|      |        |        | 80K      |                     |
|      |        | 5      | 20K      | 1.4                 |
|      |        |        | 80K      |                     |
|      | 2      | 1      | 20K      | 1.2                 |
|      |        |        | 80K      | 1.1                 |
|      | 3      | 1      | 20K      | 1.0                 |
|      |        |        | 80K      | 0.9                 |
|      |        |        | MEAN     | 1.3                 |
|      |        |        | SD       | 0.2                 |
|      |        |        | RSD (%)  | 18                  |
| Washed | 1    | 1      | 250      | ND                  |
|      | 2      | 1      | 250      | 0.018               |
|      | 3      | 1      | 250      | 0.016               |
|      |        |        | MEAN     | 0.017               |
|      |        |        | SD       | 0.001               |
|      |        |        | RSD (%)  | 8                   |

TABLE 4

ECL-Based Measurements of Sericin Content in LiSCN Dissolutions

| State | Sample | Repeat | Dil. | Sericin Content (%) |
|-------|--------|--------|------|---------------------|
| Raw   | 1      | 1      | 20K  | 1.1                 |
|       |        |        | 80K  | 1.3                 |
|       |        | 2      | 20K  | 1.0                 |
|       |        |        | 80K  | 1.7                 |
|       |        | 3      | 20K  | 1.0                 |
|       |        |        | 80K  | 1.6                 |
|       |        | 4      | 20K  | 1.0                 |
|       |        |        | 80K  | 1.5                 |
|       |        | 5      | 20K  | 1.1                 |
|       |        |        | 80K  | 1.3                 |
|       | 2      | 1      | 20K  | 1.0                 |
|       |        |        | 80K  | 1.1                 |
|       | 3      | 1      | 20K  | 1.0                 |
|       |        |        | 80K  | 1.1                 |
|       |        |        | MEAN | 1.2                 |
|       |        |        | SD   | 0.1                 |
|       |        |        | RSD (%) | 7                |
| Washed | 1     | 1      | 250  | 0.032               |
|       | 2      | 1      | 250  | 0.032               |
|       | 3      | 1      | 250  | 0.027               |
|       |        |        | MEAN | 0.030               |
|       |        |        | SD   | 0.003               |
|       |        |        | RSD (%) | 9                |

The precision of the ECL-based sericin assay for measuring the sericin content of both urea-extracted and LiSCN-dissolved silk samples was also determined and provided below in Table 5.

TABLE 5

Precision Values for ECL-Based Measurements of Sericin Content

| Sericin Prep | Sample | n | Wells Not Used | Precision (%) |
|--------------|--------|---|----------------|---------------|
| Urea         | Quads       | 17 | 16 | 6  |
|              | Repeats (5) | 10 | 16 | 7  |
|              | Samples (3) | 6  | 0  | 19 |
| LiSCN        | Quads       | 17 | 1  | 4  |
|              | Repeats (5) | 10 | 1  | 20 |
|              | Samples (3) | 6  | 0  | 9  |

If the sericin content of Ashland Bay silk is measured by the ECL-based assay following urea extraction, the raw silk has a sericin content of 0.9 to 1.6% and the washed silk has a sericin content of 0.016 to 0.018%. The precision amongst the quadruplicate wells on the ECL plates was approximately 6%. The precision for the same urea-extracted sample run five times was 7%. The precision between the three different urea-extracted samples was 19%. Accordingly, it is reasonable that the precision for the assay as a whole should reside around 15%.

If the sericin content of Ashland Bay silk is measured by the ECL-based assay following whole silk dissolution in LiSCN, the raw silk has a sericin content of 1.0 to 1.7% and the washed silk has a sericin content of 0.027 to 0.032%. The precision amongst the quadruplicate wells on the ECL plates was approximately 4%. The precision for the same urea-extracted sample run five times was 20%. The precision between the three different urea-extracted samples was 9%. Accordingly, it is reasonable that the precision for the assay as a whole should be better than 15%.

Example 4. Sericin Antigen-Down ELISA

All steps in the antigen-down ELISA assays were performed at room temperature and all reagents were allowed to reach room temperature prior to use. This sericin ELISA requires several sequential changes of reagents. Each change of reagent was accomplished by carefully inverting the microtiter plate over a sink to remove the bulk of the spent reagent. The inverted plate was then tapped on a paper towel to remove any remaining liquid.

The wells of a 96-well Immulon 2HB microtiter plate (Fischer Scientific Cat. No. 14-245-61) were accurately loaded with 100 μl sericin standard preparation, sericin peptide, or sericin sample diluted in PBS. The microtiter plate was covered with an adhesive seal and incubated for 2 hours. The sericin solution was then discarded. Each well of the microtiter plate was rinsed by filling each well with a 150 μl Wash Solution and discarding, using a micropipette. Each well of the microtiter plate was loaded with 150 μl Blocking Solution using a micropipette. The microtiter place was allowed to incubate for 30 min. The Blocking Solution was discarded, and each well of the microtiter plate was washed using the above-referenced procedure. The microtiter plate wells were accurately loaded with 110 μL of anti-sericin antibody diluted 1:20,000 in ADB. The microtiter plate was covered with an adhesive seal and incubated for 2 hours. The sericin antibody solution was discarded and each well of the microtiter plate was rinsed as before. Each well was accurately loaded with 110 μL horseradish peroxidase-conjugated, goat anti-rabbit IgG (Jackson ImmunoResearch Labs, West Grove, Pa., Cat. No. 111-035-046) diluted 1:10,000 in ADB. The microtiter plate was covered with an adhesive seal and incubated for 2 hours. The second antibody solution was discarded, and each well of the microtiter plate rinsed three times as before. The plate was incubated for 5 minutes in the third rinse. The 3,3',5,5'-tetramethyl benzidine (TMB) substrate was prepared by mixing equal volumes of TMB components A and B. 11 ml of TMB substrate were prepared per ELISA plate. The Wash Buffer was discarded and each well was accurately loaded with 105 µL of TMB substrate solution. The color was allowed to develop for 10 minutes. The color reaction was stopped by the addition of 105 µl of phosphoric acid (1M) to each well. The absorbance of each well was read at 450 nm using a microtiter plate reader (Molecular Devices VERSAmax), and the raw data were analyzed.

Figure 3:
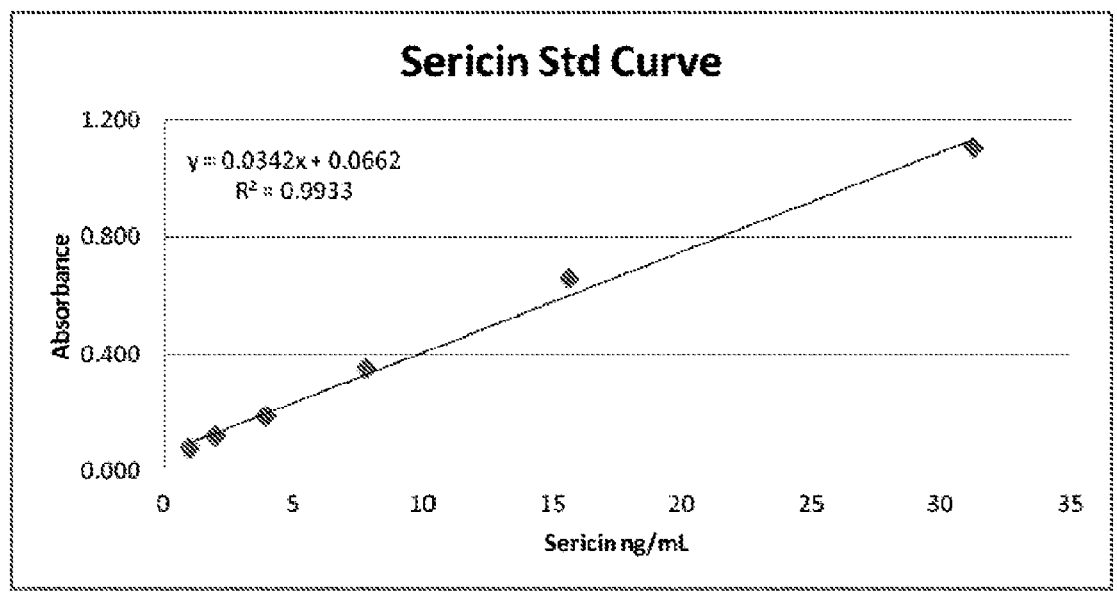
FIG. 3 is a graph showing a sericin standard curve for the sericin antigen-down ELISA, indicating that the ELISA exhibits a linear range of detection of at least 0 to 30 ng/ml, with an $R^2$ value of 0.9933.
Figure 4:
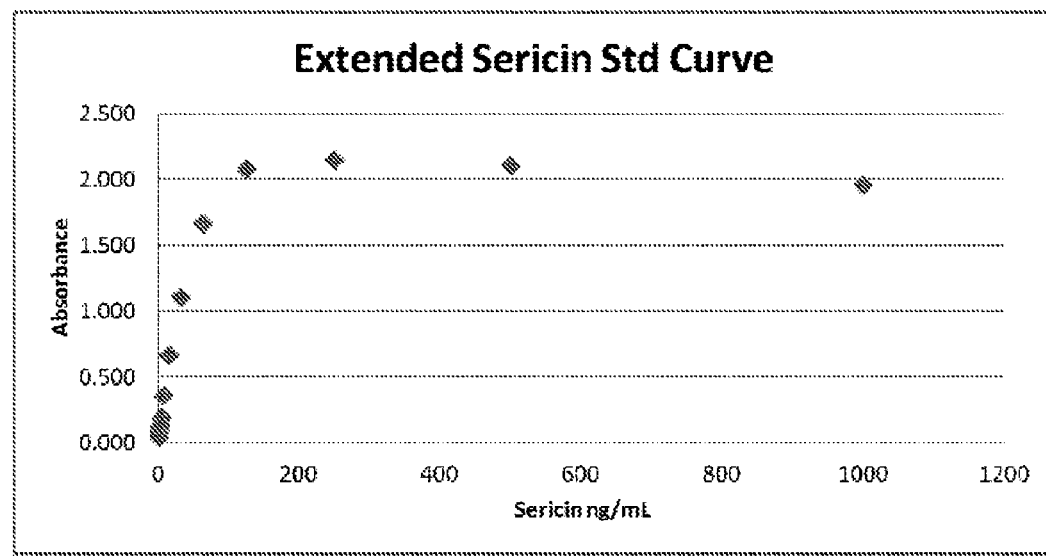
FIG. 4 is a graph showing a sericin standard curve for the sericin antigen-down ELISA, indicating that the ELISA does not exhibit a linear range of detection over a wider range from 0 to 1000 ng/ml.

If performed under the optimal conditions described above, the sericin antigen-down ELISA provides a sensitivity for sericin of greater than 1 ng/mL and exhibits a linear range of 0 to 30 ng/ml with an $R^2$ value of 0.993 (FIGS. 3 and 4). If measuring the sericin content of silk dissolved in LiSCN, a sensitivity of 1 ng/ml means that the ELISA is capable of measuring a sericin content of 0.00125%. This takes into account a silk solution dilution of 250 to negate any effect of the LiSCN on the sericin ELISA. If measuring the sericin content of silk after extraction with urea, a sensitivity of 1 ng/ml means that the ELISA is capable of measuring a sericin content of 0.0025%. Here again, this takes in to account a urea extraction dilution of 250 to negate any effect of the urea on the sericin ELISA.

The sericin ELISA was used to measure the sericin content of raw and washed Ashland Bay silk. Sericin was measured both in urea extracts and in LiSCN-dissolved silk, and the results are set forth in below in Tables 6 and 7, respectively. To provide values for assay precision, each sericin sample (dissolved or extracted) was prepared three separate times and the first sample was assayed five separate times by the antigen-down ELISA. Each ELISA measurement was made in quadruplicate.

TABLE 6

Antigen-Down ELISA Measurements of Sericin Content in Urea Extracts

| Silk | Sample | Repeat | Dilution | Sericin Content (%) |
|---|---|---|---|---|
| Raw | 1 | 1 | 20K | 1.0 |
| | | | 80K | 0.8 |
| | | 2 | 20K | 0.9 |
| | | | 80K | 0.9 |
| | | 3 | 20K | 1.1 |
| | | | 80K | 0.8 |
| | | 4 | 20K | 0.9 |
| | | | 80K | 0.9 |
| | | 5 | 20K | 1.0 |
| | | | 80K | 0.8 |
| | 2 | 1 | 20K | 0.9 |
| | | | 80K | 1.0 |
| | 3 | 1 | 20K | 0.7 |
| | | | 80K | 0.7 |
| | | | MEAN | 0.9 |
| | | | SD | 0.1 |
| | | | RSD (%) | 14 |
| Washed | 1 | 1 | 250 | ND |
| | 2 | 1 | 250 | 0.016 |
| | 3 | 1 | 250 | 0.013 |
| | | | MEAN | 0.014 |
| | | | SD | 0.002 |
| | | | RSD (%) | 15 |

TABLE 7

Antigen-Down ELISA Measurements of Sericin Content in LiSCN Dissolutions

| State | Sample | Repeat | Dil. | Sericin Content (%) |
|---|---|---|---|---|
| Raw | 1 | 1 | 20K | 1.2 |
| | | | 80K | 1.1 |
| | | 2 | 20K | 1.1 |
| | | | 80K | 1.3 |
| | | 3 | 20K | 1.1 |
| | | | 80K | 1.1 |
| | | 4 | 20K | 1.1 |
| | | | 80K | 1.3 |
| | | 5 | 20K | 1.2 |
| | | | 80K | 1.2 |
| | 2 | 1 | 20K | 1.1 |
| | | | 80K | 1.1 |
| | 3 | 1 | 20K | 1.1 |
| | | | 80K | 1.1 |
| | | | MEAN | 1.1 |
| | | | SD | 0.1 |
| | | | RSD (%) | 7 |
| Washed | 1 | 1 | 250 | 0.025 |
| | 2 | 1 | 250 | 0.025 |
| | 3 | 1 | 250 | 0.023 |
| | | | MEAN | 0.024 |
| | | | SD | 0.001 |
| | | | RSD (%) | 4 |

The precision of the antigen-down ELISA assay for measuring the sericin content of both urea-extracted and LiSCN-dissolved silk samples was also determined and provided below in Table 8.

TABLE 8

Precision Values for Antigen-Down ELISA Measurements of Sericin Content

| Sericin Prep | Sample | n | Wells Not Used | Precision (%) |
|---|---|---|---|---|
| Urea | Quads | 17 | 0 | 5 |
| | Repeats (5) | 10 | 0 | 13 |
| | Samples (3) | 6 | 0 | 17 |
| LiSCN | Quads | 17 | 1 | 4 |
| | Repeats (5) | 10 | 1 | 6 |
| | Samples (3) | 6 | 0 | 4 |

If the sericin content of Ashland Bay silk is measured by the ELISA-based assay following urea extraction, the raw silk has a sericin content of 0.7 to 1.1% and the washed silk has a sericin content of 0.013 to 0.016%. The precision amongst the quadruplicate wells on the ELISA plates was approximately 5%. The precision for the same urea-extracted sample run five times was 13%. The precision between the three different urea-extracted samples was 17%. Accordingly, it is reasonable that the precision for the assay as a whole should reside around 15%.

If the sericin content of Ashland Bay silk is measured by ELISA-based assay following whole silk dissolution in LiSCN, the raw silk has a sericin content of 1.1 to 1.3% and the washed silk has a sericin content of 0.023 to 0.025%. The precision amongst the quadruplicate wells on the ELISA plates was approximately 4%. The precision for the same urea-extracted sample run five times was 6%. The precision between the three different urea-extracted samples was 4%. Accordingly, it seems reasonable that the precision for the assay as a whole should be better than 10%.

The ELISA values obtained for sericin content by urea extraction and LiSCN dissolution are similar for raw silk (0.9 compared to 1.1%). The ELISA values obtained for sericin content by urea extraction and LiSCN dissolution are less similar for the washed silk (0.015 compared to 0.025%). Both methods suggest that the sericin content of washed silk is very low.

Example 5. Comparison of ECL-Based Sericin Assay and Antigen-Down Sericin ELISA The observed values for both the ECL-based sericin assay and antigen-down sericin ELISA are very similar with respect to the measured sericin contents and precision values. Characteristics of each sericin detection assay are set forth below in Table 9.

TABLE 9

Characteristics of ECL-Based Sericin Assay and Antigen-Down Sericin ELISA

| Characteristic | Sericin ELISA | ECL-Based Sericin Assay |
|---|---|---|
| Sensitivity | <1 ng/mL | <1 ng/mL |
| Linear range | 0-30 ng/mL | 0-2000 ng/mL |
| Sericin content, Raw silk, Urea extraction | 0.9% | 1.3% |
| Sericin content, Raw silk, LiSCN dissolution | 1.1% | 1.2% |
| Sericin content, Washed silk, Urea extraction | 0.014% | 0.017% |
| Sericin content, Washed silk, LiSCN dissolution | 0.024% | 0.030% |
| Precision, Raw silk, Urea extraction | 14% | 18% |
| Precision, Raw silk, LiSCN dissolution | 7% | 7% |
| Precision Washed silk, Urea extraction | 15% | 8% |
| Precision, Raw silk, LiSCN dissolution | 4% | 9% |
| Assay Complexity | More | Less |
| Assay Time | 7 or 8 hours | Overnight |

Importantly, both assay formats offer excellent sensitivity for sericin. Both assay formats suggest that Ashland Bay silk contains approximately 1% sericin. This is true if the sericin is measured by urea extraction or by LiSCN dissolution. Both assay formats suggest that Ashland Bay silk contains much less sericin after washing. Both assay formats suggest that washed Ashland Bay silk contains approximately 0.015% sericin when measured by urea extraction, or 0.027% when measured by LiSCN dissolution. Both assay formats offer precision values between 5 and 20%. However, the ECL-based sericin assay offers a wider linear range compared to the sericin antigen-down ELISA. This may be an advantage when measuring unknown sericin contents, as a wider range of dilutions will provide an accurate result.

Example 6. Sericin Sandwich ELISA

As demonstrated above, the antigen-down (standard) ELISA assay is sensitive and accurate, as well as rapid and robust. However, when silk (in particular, washed silk) is examined using an antigen-down ELISA format the sensitivity of the assay can be compromised because of the abundance of fibroin relative to sericin, such that very little sericin could be immobilized on the ELISA plate. This potential problem can be eliminated by the use of a sandwich ELISA, wherein a sericin capture antibody, such as one of the antibodies of the invention, is immobilized on the plate and used to "fish out" all of the available sericin from silk-containing solution. A detection antibody, which recognizes at least one spatially distinct antigenic epitope of sericin (e.g., an epitope within residues 1-1147 of sericin (SEQ ID NO: 4) or residues 1182-1186 of sericin (SEQ ID NO: 5)) can subsequently be used to enable detection of the sericin content.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents, and patent applications are herein incorporated by reference in their entirety to the same extent as if each individual publication, patent, or patent application was specifically and individually indicated to be incorporated by reference in its entirety. This application claims benefit of U.S. Provisional Ser. No. 61/953,098, filed Mar. 14, 2014, incorporated herein by reference.

What is claimed is:

1. An antibody that binds to a polypeptide at an epitope in the amino acid sequence RSHHSGVNRLLHKPGQGKICL-CFENIFDIPYHLRK (SEQ ID NO: 1).

2. The antibody of claim 1, wherein the antibody binds to a polypeptide at an epitope in the amino acid sequence RSHHSGVNRLLHKPGQGK (SEQ ID NO: 2) or KICL-CFENIFDIPYHLRK (SEQ ID NO: 3).

3. The antibody of claim 1, wherein the polypeptide is a sericin polypeptide.

4. The antibody of claim 1, wherein the antibody is a polyclonal antibody, a monoclonal antibody, a synthetic antibody, a monospecific antibody, a bispecific antibody, a multispecific antibody, or an antibody fragment that binds sericin.

5. The antibody of claim 4, wherein the antibody fragment is selected from the group consisting of Fab, Fab'-SH, Fv, scFv, and (Fab')$_2$ fragments.

6. The antibody of claim 1, wherein the antibody further comprises a diagnostic an agent.

7. The antibody of claim 6, wherein the diagnostic agent is an electrochemiluminescent (ECL) label, an enzymatic label, a fluorescent label, or a radiolabel.

8. The antibody of claim 6, wherein the diagnostic agent is directly conjugated to the antibody.

9. The antibody of claim 6, wherein the diagnostic agent is indirectly conjugated to the antibody by a linker.

10. An immunoassay kit for selectively detecting sericin in a sample, wherein the immunoassay kit comprises:
    (a) a capture antibody that binds to sericin at an epitope within residues 1148-1182 of sericin (SEQ ID NO: 1); and
    (b) a solid support.

11. The immunoassay kit of claim 10, wherein the sample or the capture antibody is immobilized on the solid support.

12. The immunoassay kit of claim 10, further comprising a detectable antibody that binds the capture antibody.

13. The immunoassay kit of claim 10, wherein the sample is silk.

14. The immunoassay kit of claim 10, wherein the solid support is a microtiter plate.

15. The immunoassay kit of claim 10, wherein the kit has a sensitivity for sericin of ≤1 ng/ml or a detection limit for sericin of ≤0.00125%.

16. A method for selectively detecting sericin in a sample, the method comprising the steps of:
    (a) immobilizing the sample to a solid support to form an immobilized sample;
    (b) contacting the immobilized sample with a capture antibody to form an immobilized sericin-capture antibody complex, wherein the capture antibody binds to sericin at an epitope within residues 1148-1182 of sericin (SEQ ID NO: 1);
    (c) separating unbound capture antibody from the immobilized sericin-capture antibody complex; and
    (d) measuring the level of sericin bound to the capture antibody using a detection means for the capture antibody.

17. The method of claim 16, wherein the sample is silk.

18. The method of claim 16, wherein the solid support is a microtiter plate.

19. The method of claim 16, wherein the method has a sensitivity for sericin of ≤1 ng/ml or a detection limit for sericin of ≤0.00125%.

20. A method for inserting an implantable composition comprising silk into a subject, the method comprising:
    (a) providing silk fibers, wherein the silk fibers have a sericin content of ≤0.5% (w/w) measured using the method of claim 16 or the immunoassay kit of claim 10, (b) incorporating the silk fibers into the implantable composition, and (c) inserting the implantable composition into the subject.

21. A method for inserting an implantable composition comprising silk into a subject, the method comprising:
   (a) providing an implantable composition comprising silk, wherein the silk has a sericin content of ≤0.5% (w/w) measured using the method of claim 16 or the immunoassay kit of claim 10,
   (b) inserting the implantable composition into the subject.

22. A method for determining whether a batch of silk is suitable for medical use, the method comprising:
   (a) providing a batch of silk, wherein the silk has a sericin content measured using the method of claim 16 or the immunoassay kit of claim 10,
   (b) on the basis of the sericin content, determining whether the batch of silk is suitable for medical use.

23. A method for implanting a pliable implantable composition into a subject, the pliable implantable composition comprising:
   (a) from 5% to 20% (w/w) a dispersing agent selected from glycerin, polyethylene glycol, N-methyl pyrrolidone, and triacetin;
   (b) from 1.0% to 6.0% (w/w) a polymer selected from sodium carboxymethylcellulose, polyvinylalcohol, hydroxyethyl cellulose, hydroxypropyl methylcellulose, methylcellulose, ethylcellulose, and hyaluronic acid;
   (c) from 65% to 90% (w/w) particulate bone graft substitute or particulate demineralized bone matrix having a mean particle size of from 100 μm to 1000 μm; and
   (d) from 0.2% to 3.5% (w/w) silk fibers, the silk fibers having (i) an average length of from 0.5 to 15 mm and (ii) a sericin content of ≤0.5% (w/w) measured using the method of claim 16 or the immunoassay kit of claim 10,
   wherein the method comprises inserting the pliable implantable composition into the subject at an osteogenic site.

24. A method for determining whether a batch of silk is suitable for use in a skin care, hair care, or hair coloring composition, the method comprising:
   (a) providing a batch of silk, wherein the silk has a sericin content measured using the method of claim 16 or the immunoassay kit of claim 10, and
   (b) on the basis of the sericin content, determining whether the batch of silk is suitable for use in the skin care, hair care, or hair coloring composition.

25. A method for cryoprotecting cells, the method comprising:
   (a) providing a serum-free freezing medium, the serum-free freezing medium comprising sericin, wherein the sericin is substantially free of fibroin as measured using the method of claim 16 or the immunoassay kit of claim 10;
   (b) resuspending the cells with the serum-free freezing medium in a cryovial; and
   (c) freezing the cryovial.

26. A method for selectively detecting sericin in a sample, the method comprising the steps of:
   (a) immobilizing the sample to a solid support to form an immobilized sample;
   (b) contacting the immobilized sample with a capture antibody to form an immobilized sericin-capture antibody complex, wherein the capture antibody binds to sericin at an epitope within residues 1148-1182 of sericin (SEQ ID NO: 1);
   (c) separating unbound capture antibody from the immobilized sericin-capture antibody complex;
   (d) contacting the immobilized sericin-capture antibody complex with a detectable antibody that binds the capture antibody to form an immobilized sericin-capture antibody-detectable antibody complex;
   (e) separating unbound detectable antibody from the immobilized sericin-capture antibody-detectable antibody complex; and
   (f) measuring the level of sericin bound to the capture antibody using a detection means for the detectable antibody.

27. A method for selectively detecting sericin in a sample, the method comprising the steps of:
   (a) immobilizing a capture antibody to a solid support to form an immobilized capture antibody, wherein the capture antibody binds to sericin at an epitope within residues 1148-1182 of sericin (SEQ ID NO: 1);
   (b) contacting the immobilized capture antibody with the sample to form an immobilized capture antibody-sericin complex;
   (c) separating unbound sample from the immobilized capture antibody-sericin complex;
   (d) contacting the immobilized capture antibody-sericin complex with a detectable antibody that binds to sericin at an epitope within residues 1-1147 of sericin (SEQ ID NO: 4) or residues 1182-1186 of sericin (SEQ ID NO: 5) to form an immobilized capture antibody-sericin-detectable antibody complex;
   (e) separating unbound detectable antibody from the immobilized capture antibody-sericin-detectable antibody complex; and
   (f) measuring the level of sericin bound to the capture antibody using a detection means for the detectable antibody.

\* \* \* \* \*

UNITED STATES PATENT AND TRADEMARK OFFICE
CERTIFICATE OF CORRECTION

PATENT NO. : 9,745,370 B2  
APPLICATION NO. : 15/125780  
DATED : August 29, 2017  
INVENTOR(S) : James J. Benedict et al.

Page 1 of 1

It is certified that error appears in the above-identified patent and that said Letters Patent is hereby corrected as shown below:

In the Claims

Column 35, Line 52, in Claim 6, replace "comprises a diagnostic an agent" with --comprises a diagnostic agent--.

Column 37, Line 9, in Claim 21, replace "immunoassay kit of claim 10" with --immunoassay kit of claim 10, and--;
        Line 15, in Claim 22, replace "immunoassay kit of claim 10," with --immunoassay kit of claim 10, and--.

Signed and Sealed this  
Twenty-seventh Day of November, 2018

Andrei Iancu  
*Director of the United States Patent and Trademark Office*

SEQUENCE LISTING

<160> NUMBER OF SEQ ID NOS: 5

<210> SEQ ID NO 1
<211> LENGTH: 35
<212> TYPE: PRT
<213> ORGANISM: Artificial Sequence
<220> FEATURE:
<223> OTHER INFORMATION: Synthetic Construct

<400> SEQUENCE: 1

Arg Ser His His Ser Gly Val Asn Arg Leu Leu His Lys Pro Gly Gln
1               5                   10                  15

Gly Lys Ile Cys Leu Cys Phe Glu Asn Ile Phe Asp Ile Pro Tyr His
            20                  25                  30

Leu Arg Lys
        35

<210> SEQ ID NO 2
<211> LENGTH: 18
<212> TYPE: PRT
<213> ORGANISM: Artificial Sequence
<220> FEATURE:
<223> OTHER INFORMATION: Synthetic Construct

<400> SEQUENCE: 2

Arg Ser His His Ser Gly Val Asn Arg Leu Leu His Lys Pro Gly Gln
1               5                   10                  15

Gly Lys

<210> SEQ ID NO 3
<211> LENGTH: 18
<212> TYPE: PRT
<213> ORGANISM: Artificial Sequence
<220> FEATURE:
<223> OTHER INFORMATION: Synthetic Construct

<400> SEQUENCE: 3

Lys Ile Cys Leu Cys Phe Glu Asn Ile Phe Asp Ile Pro Tyr His Leu
1               5                   10                  15

Arg Lys

<210> SEQ ID NO 4
<211> LENGTH: 1147
<212> TYPE: PRT
<213> ORGANISM: Artificial Sequence
<220> FEATURE:
<223> OTHER INFORMATION: Synthetic Construct

<400> SEQUENCE: 4

Met Arg Phe Val Leu Cys Cys Thr Leu Ile Ala Leu Ala Ala Leu Ser
1               5                   10                  15

Val Lys Ala Phe Gly His His Pro Gly Asn Arg Asp Thr Val Glu Val
                20                  25                  30

Lys Asn Arg Lys Tyr Asn Ala Ala Ser Ser Glu Ser Ser Tyr Leu Asn
            35                  40                  45

Lys Asp Asn Asp Ser Ile Ser Ala Gly Ala His Arg Ala Lys Ser Val
50                  55                  60

Glu Gln Ser Gln Asp Lys Ser Lys Tyr Thr Ser Gly Pro Glu Gly Val
65                  70                  75                  80

Ser Tyr Ser Gly Arg Ser Gln Asn Tyr Lys Asp Ser Lys Gln Ala Tyr
                85                  90                  95

Ala Asp Tyr His Ser Asp Pro Asn Gly Ser Ala Ser Ala Gly Gln
                100                 105                 110

Ser Arg Asp Ser Ser Leu Arg Glu Arg Asn Val His Tyr Val Ser Asp
            115                 120                 125

Gly Glu Ala Val Ala Ala Ser Ser Asp Ala Arg Asp Glu Asn Arg Ser
130                 135                 140

Ala Gln Gln Asn Ala Gln Ala Asn Trp Asn Ala Asp Gly Ser Tyr Gly
145                 150                 155                 160

Val Ser Ala Asp Arg Ser Gly Ser Ala Ser Arg Arg Gln Ala
                165                 170                 175

Asn Tyr Tyr Ser Asp Lys Asp Ile Thr Ala Ala Ser Lys Asp Asp Ser
            180                 185                 190

Arg Ala Asp Ser Ser Arg Arg Ser Asn Ala Tyr Tyr Asn Arg Asp Ser
        195                 200                 205

-continued

```
Asp Gly Ser Glu Ser Ala Gly Leu Ser Asp Arg Ser Ala Ser Ser Ser
    210                 215                 220
Lys Asn Asp Asn Val Phe Val Tyr Arg Thr Lys Asp Ser Ile Gly Gly
225                 230                 235                 240
Gln Ala Lys Ser Ser Arg Ser Ser His Ser Gln Glu Ser Asp Ala Tyr
                245                 250                 255
Tyr Asn Ser Ser Pro Asp Gly Ser Tyr Asn Ala Gly Thr Arg Asp Ser
                260                 265                 270
Ser Ile Ser Asn Lys Lys Lys Ala Ser Ser Thr Ile Tyr Ala Asp Lys
                275                 280                 285
Asp Gln Ile Arg Ala Ala Asn Asp Arg Ser Ser Ser Lys Gln Leu Lys
    290                 295                 300
Gln Ser Ser Ala Gln Ile Ser Ser Gly Pro Glu Gly Thr Ser Val Ser
305                 310                 315                 320
Ser Lys Asp Arg Gln Tyr Ser Asn Asp Lys Arg Ser Lys Ser Asp Ala
                325                 330                 335
Tyr Val Gly Arg Asp Gly Thr Val Ala Tyr Ser Asn Lys Asp Ser Glu
                340                 345                 350
Lys Thr Ser Arg Gln Ser Asn Thr Asn Tyr Ala Asp Gln Asn Ser Val
                355                 360                 365
Arg Ser Asp Ser Ala Ala Ser Asp Gln Thr Ser Lys Ser Tyr Asp Arg
    370                 375                 380
Gly Tyr Ser Asp Lys Asn Ile Val Ala His Ser Ser Gly Ser Arg Gly
385                 390                 395                 400
Ser Gln Asn Gln Lys Ser Ser Ser Tyr Arg Ala Asp Lys Asp Gly Phe
                405                 410                 415
Ser Ser Ser Thr Asn Thr Glu Lys Ser Lys Phe Ser Ser Ser Asn Ser
                420                 425                 430
Val Val Glu Thr Ser Asp Gly Ala Ser Ala Ser Arg Glu Ser Ser Ala
    435                 440                 445
Glu Asp Thr Lys Ser Ser Asn Ser Asn Val Gln Ser Asp Glu Lys Ser
    450                 455                 460
Ala Ser Gln Ser Ser Ser Ser Arg Ser Ser Gln Glu Ser Ala Ser Tyr
465                 470                 475                 480
Ser Ser Ser Ser Ser Ser Thr Leu Ser Glu Asp Ser Ser Glu Val
                485                 490                 495
Asp Ile Asp Leu Gly Asn Leu Gly Trp Trp Asn Ser Asp Asn Lys
                500                 505                 510
Val Gln Arg Ala Ala Gly Gly Ala Thr Lys Ser Gly Ala Ser Ser Ser
                515                 520                 525
Thr Gln Ala Thr Thr Val Ser Gly Ala Asp Asp Ser Ala Asp Ser Tyr
    530                 535                 540
Thr Trp Trp Asn Pro Arg Arg Ser Ser Ser Ser Ser Ser Ala
545                 550                 555                 560
Ser Ser Ser Ser Ser Gly Ser Asn Val Gly Gly Ser Gln Ser Ser
                565                 570                 575
Gly Ser Ser Thr Ser Gly Ser Asn Ala Arg Gly His Leu Gly Thr Val
                580                 585                 590
Ser Ser Thr Gly Ser Thr Ser Asn Thr Asp Ser Ser Lys Ser Ala
    595                 600                 605
Gly Ser Arg Thr Ser Gly Gly Ser Ser Thr Tyr Gly Tyr Ser Ser Ser
    610                 615                 620
His Arg Gly Gly Ser Val Ser Ser Thr Gly Ser Ser Ser Asn Thr Asp
```

```
            625                 630                 635                 640
Ser Ser Thr Lys Asn Ala Gly Ser Ser Thr Ser Gly Gly Ser Ser Thr
                645                 650                 655

Tyr Gly Tyr Ser Ser His Arg Gly Gly Ser Val Ser Ser Thr Gly
            660                 665                 670

Ser Ser Ser Asn Thr Asp Ser Ser Thr Lys Ser Ala Gly Ser Ser Thr
                675                 680                 685

Ser Gly Gly Ser Ser Thr Tyr Gly Tyr Ser Ser Arg His Arg Gly Gly
            690                 695                 700

Arg Val Ser Ser Thr Gly Ser Ser Ser Thr Thr Asp Ala Ser Ser Asn
705                 710                 715                 720

Ser Val Gly Ser Ser Thr Ser Gly Gly Ser Ser Thr Tyr Gly Tyr Ser
                725                 730                 735

Ser Asn Ser Arg Asp Gly Ser Val Ser Ser Thr Gly Ser Ser Ser Asn
                740                 745                 750

Thr Asp Ser Asn Ser Asn Ser Ala Gly Ser Ser Thr Ser Gly Gly Ser
                755                 760                 765

Ser Thr Tyr Gly Tyr Ser Ser Asn Ser Arg Asp Gly Ser Val Ser Ser
            770                 775                 780

Thr Gly Ser Ser Ser Asn Thr Asp Ser Asn Ser Asn Ser Ala Gly Ser
785                 790                 795                 800

Ser Thr Ser Gly Gly Ser Ser Thr Tyr Gly Tyr Ser Ser Asn Ser Arg
                805                 810                 815

Asp Gly Ser Val Ser Ser Thr Gly Ser Ser Ser Asn Thr Asp Ala Ser
            820                 825                 830

Thr Asp Leu Thr Gly Ser Ser Thr Ser Gly Gly Ser Ser Thr Tyr Gly
            835                 840                 845

Tyr Ser Ser Asp Ser Arg Asp Gly Ser Val Ser Ser Thr Gly Ser Ser
            850                 855                 860

Ser Asn Thr Asp Ala Ser Thr Asp Leu Ala Gly Ser Ser Thr Ser Gly
865                 870                 875                 880

Gly Ser Ser Thr Tyr Gly Tyr Ser Ser Asp Cys Gly Asp Gly Ser Val
                885                 890                 895

Ser Ser Thr Gly Ser Ser Ser Asn Thr Asp Ala Ser Thr Asp Leu Ala
                900                 905                 910

Gly Ser Ser Thr Ser Gly Gly Ser Ser Thr Tyr Gly Tyr Ser Ser Asp
            915                 920                 925

Ser Arg Asp Gly Ser Val Ser Ser Thr Gly Ser Ser Ser Asn Thr Asp
            930                 935                 940

Ala Ser Thr Asp Leu Ala Gly Ser Ser Thr Ser Gly Gly Ser Ser Thr
945                 950                 955                 960

Tyr Gly Tyr Ser Ser Asn Ser Arg Asp Gly Ser Val Ser Ser Thr Gly
                965                 970                 975

Ser Ser Ser Asn Thr Asp Ala Ser Thr Asp Leu Thr Gly Ser Ser Thr
                980                 985                 990

Ser Gly Gly Ser Ser Thr Tyr Gly Tyr Ser Ser Ser Asn Arg Asp Gly
            995                 1000                1005

Ser Val Leu Ala Thr Gly Ser Ser Asn Thr Asp Ala Ser Thr
            1010                1015                1020

Thr Glu Glu Ser Thr Thr Ser Ala Gly Ser Ser Thr Glu Gly Tyr
            1025                1030                1035

Ser Ser Ser Ser His Asp Gly Ser Val Thr Ser Thr Asp Gly Ser
            1040                1045                1050
```

```
Ser Thr Ser Gly Gly Ala Ser  Ser Ser Ser Ala Ser  Thr Ala Lys
    1055                1060             1065

Ser Asp Ala Ala Ser Ser Glu  Asp Gly Phe Trp Trp  Trp Asn Arg
    1070                1075             1080

Arg Lys Ser Gly Ser Gly His  Lys Ser Ala Thr Val  Gln Ser Ser
    1085                1090             1095

Thr Thr Asp Lys Thr Ser Thr  Asp Ser Ala Ser Ser  Thr Asp Ser
    1100                1105             1110

Thr Ser Ser Thr Ser Gly Ala  Ser Thr Thr Thr Ser  Gly Ser Ser
    1115                1120             1125

Ser Thr Ser Gly Gly Ser Ser  Thr Ser Asp Ala Ser  Ser Thr Ser
    1130                1135             1140

Ser Ser Val Ser
    1145

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Lys Asn Ile Gly Val
1               5
```